US006512236B2

(12) United States Patent
Seville

(10) Patent No.: US 6,512,236 B2
(45) Date of Patent: Jan. 28, 2003

(54) FLUOROMETRIC DETECTION USING VISIBLE LIGHT

(75) Inventor: Mark Seville, Denver, CO (US)

(73) Assignee: Clare Chemical Research, Inc., Dolores, CO (US)

( * ) Notice: Subject to any disclaimer, the term of this patent is extended or adjusted under 35 U.S.C. 154(b) by 25 days.

(21) Appl. No.: 09/753,783

(22) Filed: Jan. 2, 2001

(65) Prior Publication Data

US 2002/0089658 A1 Jul. 11, 2002

Related U.S. Application Data

(63) Continuation of application No. 09/036,034, filed on Mar. 6, 1998, now Pat. No. 6,198,107.
(60) Provisional application No. 60/040,124, filed on Mar. 7, 1997.

(51) Int. Cl.$^7$ .............................................. G01N 21/64
(52) U.S. Cl. .................................. 250/458.1; 250/459.1
(58) Field of Search ........................... 250/458.1, 459.1

(56) References Cited

U.S. PATENT DOCUMENTS

| 3,802,102 A | 4/1974 | Licciardi ................... 40/132 R |
| 4,071,883 A | 1/1978 | Dennis ......................... 362/97 |
| 4,117,338 A | 9/1978 | Adrion et al. .......... 250/461 R |
| 4,906,100 A | 3/1990 | Rice et al. .................... 356/417 |
| 5,108,179 A | 4/1992 | Myers ......................... 356/344 |
| 5,274,240 A | 12/1993 | Mathies et al. .......... 250/458.1 |
| 5,315,375 A | 5/1994 | Allen .......................... 356/417 |
| 5,327,195 A | 7/1994 | Ehr ............................. 355/113 |
| 5,347,342 A | 9/1994 | Ehr ............................. 355/113 |
| 5,363,854 A | 11/1994 | Martens et al. ............. 128/665 |
| 5,387,801 A | 2/1995 | Gonzalez et al. ........ 250/504 R |
| 5,543,018 A | 8/1996 | Stevens et al. .............. 204/461 |
| 5,736,744 A | 4/1998 | Johannsen et al. ........ 250/505.1 |
| 5,856,866 A | 1/1999 | Shimizu et al. ................ 356/73 |
| 6,161,323 A | * 12/2000 | Kageyama ................... 43/17.5 |
| 6,198,107 B1 | * 3/2001 | Seville ..................... 250/458.1 |

FOREIGN PATENT DOCUMENTS

| EP | 0 603 783 A1 | 6/1994 | .......... G01N/33/52 |
| JP | 10-132744 | 5/1998 | .......... G01N/21/64 |
| JP | 10-274637 | 10/1998 | .......... G01N/27/447 |

OTHER PUBLICATIONS

UVP International Ultra–Violet Products, (Feb. 1990), "New Products," UVP International Newsletter, 4 pp.
Herolab GMBH, (Aug 1995), "Produktkatalog," *Herolab Highlights*, 1:1–7, XP002158317.

(List continued on next page.)

Primary Examiner—Constantine Hannaher
(74) Attorney, Agent, or Firm—Greenlee, Winner and Sullivan, P.C.

(57) ABSTRACT

Systems, devices and methods are provided for viewing a pattern of fluorophors capable of fluorescing when exposed to visible light, e.g., fluorescently stained DNA, protein or other biological material. The system includes a light source emitting light in the visible spectrum, such as a fluorescent lamp used in domestic lighting, a first optical filter capable of transmitting light from the source at wavelengths capable of exciting the fluorophors and of absorbing light of other wavelengths, and a second optical filter capable of blocking substantially all the light from the source not blocked by the first filter, so that the only light reaching the viewer is light produced by fluorescence of the fluorophors.

74 Claims, 17 Drawing Sheets

OTHER PUBLICATIONS

Brunk, C.F. and Simpson, L., (Oct 1977), "Comparison of Various Ultraviolet Sources for Fluorescent Detection of Ethidium Bromide–DNA Complexes in Polyacrylamide Gels,"*Analytical Biochemistry* 82:455–462.

Golden, Gregory S., (May 1994), Use of Alternative Light Source Illumination in Bite Mark Photography, *J. Forensic Sciences,* 39:815–823.

Gründemann, D. and Schömig, E., (Nov 1996), "Protection of DNA During Preparative Agarose Gel Electrophoresis Against Damage Induced by Ultraviolet Light," *BioTechniques* 21:898–903.

Haughland, R. P., "Hand Book of Fluorescent Probes and Research Chemicals," (1996) $6_{th}$Edition, Michelle T.Z. Spence, Ed., Molecular Probes Inc. Eugene OR, pp. 13–18, 25–28 and 29–35.

Menzel, E.R., (1991), "An Introduction to Lasers, Forensic Lights and Fluorescent Fingerprint Detection Techniques," *Lightning Powder Company, Inc., Salem OR.*

Neri et al., (Apr 1996), "Multipurpose High Sensitivity Luminescence Analyzer(LUANA): Use in Gel Electrophoresis," *BioTechniques* 20(4):708–713.

Payton Scientific Inc. website—*http://home.att.net/~paytonscientific/page6.html,* pp. 1–2, date of publication unknown (downloaded Jul. 21, 1999).

Payton Scientific Inc, website—*http://home.ztt.net/~paytonscientific/page14.html,* pp. 1–2, date of publication unknown (downloaded Jul. 21, 1999).

Payton Scientific Inc. website—*http://home.att.net/~paytonscientific/page7.html.* pp. 1–2, date of publication unknown (downloaded Jul. 21, 1999).

Payton Scientific Inc. website—*http://home.att.net/~paytonscientific/page8.html.* pp. 1–2, date of publication unknown (downloaded Jul. 21, 1999).

Payton Scientific Inc. website—*http:/~paytonscientific/index.html.* pp. 1–3, date of publication unknown (downloaded Jul. 21, 1999).

Rofin Forensic Products website—*http://rofin.com.au/pr—fp.htm.* pp. 1–8, date of publication unknown (downloaded Jul. 6, 1999).

Sharp, P.A. et al., (1973), "Detection of Two Restriction Endonucleases Activities in *Haemophilus parainfluenzae* Using Analytical Agarose–Ethidium Bromide Electrophoresis," *Biochemistry* 12(16):3055–3063.

Stoilovic, Milutin, (1991), "Detection of Semen and Blood Stains Using Pololight as a Light Source," *Forensic Science International* 51:289–296.

Ünlüet al., (Oct. 1997), "Difference gel electrophoresis: A single gel method for detecting changes in protein extracts, "*Electrophoresis* 18:2071–2077.

\* cited by examiner

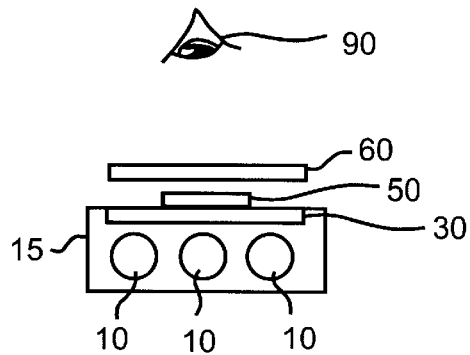
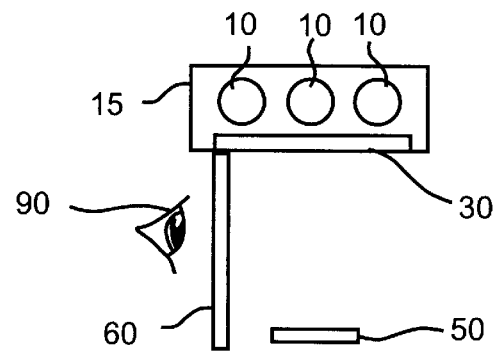
FIG. 13  FIG. 14
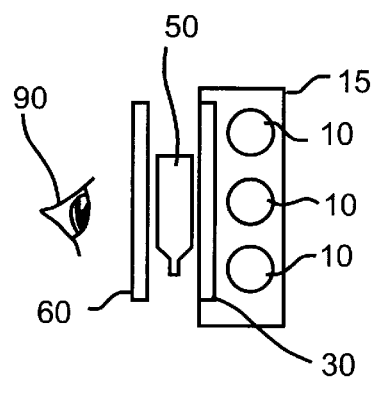
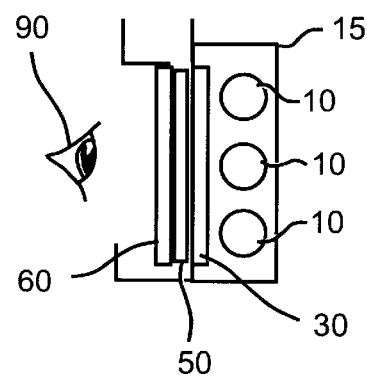
FIG. 15  FIG. 16

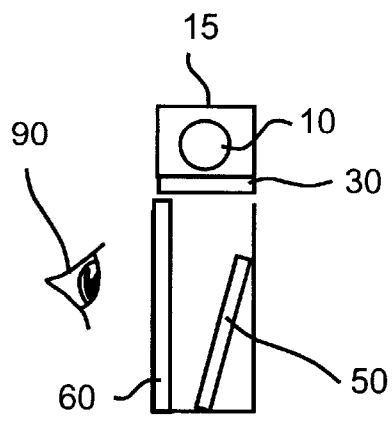
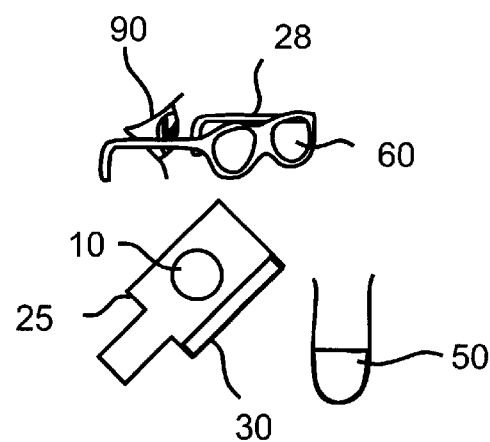
FIG. 17    FIG. 18
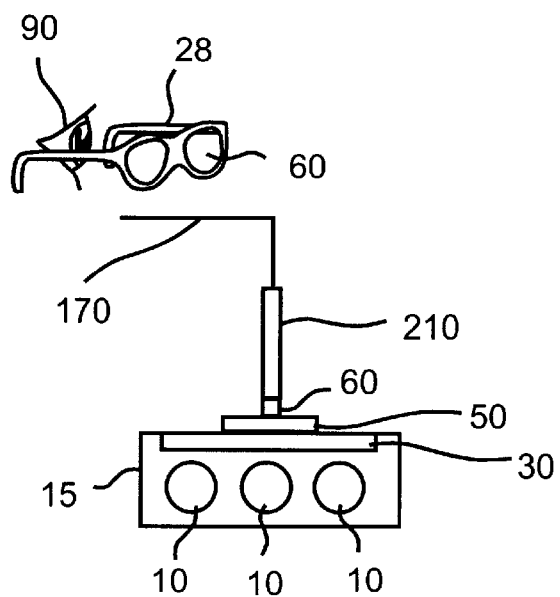
FIG. 19

FLUOROMETRIC DETECTION USING VISIBLE LIGHT

CROSS-REFERENCE TO RELATED APPLICATIONS

This application is a continuation of co-pending U.S. Ser. No. 09/036,034 filed Mar. 6, 1998, now U.S. Pat. No. 6,198,107 which claims priority to U.S. Ser. No. 60/040,124 filed Mar. 7, 1997, incorporated herein by reference to the extent not inconsistent herewith.

BACKGROUND OF THE INVENTION

The separation of DNA fragments by polyacrylamide or agarose gel electrophoresis is a well-established and widely used tool in molecular biology (Sharp, P.A. et al., "Detection of two restriction endonucleases activities in *Haemophilus parainfluenzae* using analytical agarose-ethidium bromide electrophoresis," (1973) *Biochemistry* 12:3055). The standard technique for viewing the positions of the separated fragments in a gel involves the use of an ultra-violet (UV) transilluminator (Brunk, C. F. and Simpson, L., "Comparison of various ultraviolet sources for fluorescent detection of ethidium bromide-DNA complexes in polyacrylamide gels," (1977) *Analytical Biochemistry* 82:455). This procedure involves first staining the gel with a fluorescent dye such as ethidium bromide or SYBR® Green I. The DNA fragments, which bind the dye, are then visualized by placing the gel on a light-box equipped with a UV light-source. Typically the UV source, in combination with a built-in filter, provides light with an excitation maximum of around 254, 300 or 360 nm. The UV light causes the DNA-bound dye to fluoresce in the red (ethidium bromide) or green (SYBR Green I) regions of the visible light spectrum. The colored fluorescence allows visualization and localization of the DNA fragments in the gel. The visualization of DNA in a gel is used either to assess the success of a gene cloning reaction as judged by the size and number of DNA fragments present, or to identify a particular sized fragment which can be cut out from the gel and used in further reaction steps.

Transilluminators used in the art to visualize fluorophors are described in a number of patents, including U.S. Pat. Nos. 5,347,342, 5,387,801, 5,327,195, 4,657,655, and 4,071,883. Clinical examination of skin anomalies causing fluorescence have been described in U.S. Pat. No. 5,363,854 using visible light images as a control.

The use of UV light for viewing molecules in gels has two major disadvantages: (1) It is dangerous. The eyes are very sensitive to UV light and it is an absolute necessity that the viewer wear eye-protection, even for brief viewing periods, to prevent the possibility of serious damage. More prolonged exposure to UV light results in damage to the skin tissues (sunburn) and care must be taken to minimize skin exposure by wearing gloves, long-sleeved jackets and a full-face mask. (2) DNA samples are damaged by exposure to UV light. It has recently been documented by Epicentre Technologies that a 10–20 second exposure to 305 nm UV light on a transilluminator is sufficient to cause extensive damage to the DNA. This period of time is the absolute minimum required to excise a DNA band from a gel.

An alternative to UV transillumination involves the use of laser light sources. However, the use of laser light is not applicable to the simple and direct viewing of a DNA gel by the human eye. The extremely small cross-section of the laser light beam requires that a typical DNA gel be scanned by the laser, the fluorescence intensity at each point measured electronically and stored digitally before a composite picture of the DNA gel is assembled for viewing using computer software.

Visible light boxes for artists' uses are known to the art for visualizing non-fluorescing materials, e.g., as described in U.S. Pat. No. 3,802,102. The use of visible light to detect certain fluorescent dyes is suggested, e.g., in Lightools Research web page. However, no enabling disclosure for making such devices is provided. None of these references provides devices or systems for viewing fluorescence patterns using visible light.

Despite the recent development of dyes fluorescing in the visible spectrum (Haugland, R. [1996] "Handbook of Fluorescent Probes and Research Chemicals, Sixth Edition," Molecular Probes, Inc., Eugene, Oreg., pp. 13–18, 25–29, 29–35), transilluminators and other devices to take advantage of the properties of such dyes have not been made available to the public. It is an object of this invention to provide devices and methods for directly and indirectly viewing and measuring patterns of fluorescence not involving the use of UV transillumination but rather being capable of using sources of visible light such as ordinary lamps, as opposed to lasers and the focused lights used in standard fluorometers.

All publications referred to herein are incorporated by reference.

SUMMARY

A visible light system is provided for detection of patterns of fluorescence emitted by fluorophors capable of emitting light of an emitted wavelength range (emission spectrum) when excited by light of an excitation wavelength range (excitation spectrum). In one embodiment, the excitation wavelength range must be different from the emitted wavelength range, although these ranges may overlap, and at least a portion of the non-overlapping portion of the emitted wavelength range must be within the visible spectrum. Both the exciting and emitted wavelength ranges are within the visible spectrum.

In preferred embodiments, using color filters, light of the "excitation type" for the fluorophor is light within the excitation wavelength range for the fluorophor, and light of the "emitted type" is light within the emitted wavelength range for the fluorophor. The first filter preferably transmits at least about 70% of the light from the light source in the excitation wavelength range, and the second filter transmits at least about 95% of the light in the emitted wavelength range. The term "filter" as used herein includes combinations of filters.

In other embodiments using polarizing filters, the first filter transmits the light from the source in a narrow range of orientations, and the second filter is oriented to exclude light from the source, i.e., transmits only light orthogonal to that passed by the first filter, so that only light emitted by the fluorophor passes through the second filter.

This invention comprises a visible light system comprising:
 a) a light source capable of producing visible light of the excitation type for the fluorophors;
 b) a first optical filter placed between said light source and said fluorophors, which is capable of transmitting light from said light source of the excitation type for said fluorophors and of preventing transmission of at least a portion of the light from said light source of said emitted type; and
 c) a second optical filter placed between said fluorophors and a light detector which second filter is capable of transmitting light of said emitted type and of preventing transmission of light from said light source of said excitation type, to form a viewable image of the pattern of fluorophors.

The fluorophors may be any fluorophors known or readily available to those skilled in the art, and are preferably used in the form of fluorophors bound to or in a biological sample. Fluorophors may be used to detect and quantify any desired substance to which they can be attached or into which they can be incorporated, e.g. organic molecules such as proteins, nucleic acids, carbohydrates, pigments, and dyes, inorganic molecules such as minerals, bacteria, eukaryotic cells, tissues and organisms. Fluorophors may also be an intrinsic part of an organism or substance to be detected, e.g., various dyes and pigments found in, for example, fungi, fish, bacteria and minerals.

The system of this invention may be incorporated into an integrated device such as a horizontal or vertical gel electrophoresis unit, scanner or other device in which detection of fluorescence is required.

The devices and methods of this invention are especially useful for viewing patterns, i.e., two-dimensional and three-dimensional spatial arrangements of fluorophors. Fluorescence detectors such as found in fluorometers are able to detect only the presence and intensity of fluorescence, and rather than generating an image generate a stream of data which must be interpreted by machine. The present invention allows direct viewing of two-dimensional (or three-dimensional) patterns of fluorophors by the human eye. Such patterns of fluorophors include the spatial arrangement of fluorophors on DNA on a gel, or of fluorophors on a TLC plate, the spatial distribution of fluorophors in test tubes in a rack, the spatial distribution of fluorophors in fungus or bacteria on skin, or on meat meant for human consumption, or the spatial arrangement of fluorescent fish in a tank. The images of patterns of fluorescence generated by the methods and devices of this invention may be viewed over time and may be photographed, digitized, stored and otherwise manipulated by machine but, in all cases, a two- or three-dimensional image is generated. The light source should not be a laser, and any mechanical detector used herein, like the human eye, preferably includes an array of photodetectors.

The light source should produce minimal light in the ultraviolet range, i.e., less than 1% of its light should be in the ultraviolet range, or the first filter should effectively screen out ultraviolet light, preferably to a level less than 1%, to prevent damage to DNA being viewed in the system. Even when using polarizing filters, a blue filter is preferably used as part of or in addition to the first filter to prevent DNA damage. Alternatively, the diffuser may be used to filter out residual UV light, and the diffuser and first filter can be combined into one sheet of material. (Most blue filters filter out ultraviolet light as well as visible light in wavelengths longer than blue.)

The light detector or "viewer" used to detect the fluorescence of the fluorophor using this system may be a viewer's eye, or a device such as an optical scanner or charge coupled device camera for inputting a digitized image into a computer, or a camera. Such devices may also comprise means for quantifying the light within the emitted wavelength range reaching the viewer, and may also comprise means, such as a properly programmed computer as is known to the art, for converting such quantitative measurements to values for the amount of biological material present in the sample being measured.

The first filter is capable of filtering out light from the light source of the emitted type for the fluorophors. This means that at least some of the light from the light source of the emitted type is filtered out by the first filter. In many cases, the excitation and emission spectra for the fluorophors being used overlap. The first filter need only absorb light in a portion of the emission spectrum, usually the upper wavelength end thereof.

In some embodiments, the first filter may be an integral part of the support for the fluorophor or of the material or medium containing the fluorophor. For example, the first filter may serve as the gel support of a transilluminator device on which fluorophor-containing material in gel is placed. The gel itself, e.g., impregnated with pigment such as blue pigment, may serve as the first filter.

In some embodiments, as more fully described below, the second filter may be adapted to be placed over the human eye, e.g. as lenses for glasses to be worn by a human viewer, or may be adapted to be attached to the lens of an optical scanner or camera. The second filter may also serve as a safety lid for an electrophoresis unit or as a wall for the container for the fluorophor-containing material. The term "attached" in this context means both removably attached or built in as an integral part of a device. Also in some embodiments described below, the light source may be a handheld light source held behind the sample or preferably in front of the sample and at an angle to the viewer. The handheld unit for holding the light source also preferably comprises the first optical filter as part of the casing.

The fluorophor-containing material may be transparent or opaque, and the system may be configured to allow light from the light source to pass directly through the first filter, the fluorophor-containing material, and the second filter to reach the viewer in the case of a transparent medium, or to allow light from the light source to pass through the first filter to strike the fluorophor-containing material, allowing emitted light to "bounce" back from the medium toward the viewer, first passing through the second filter. The configuration of optical components may occupy any angle from just over 0° to 180°. The angle is that formed by lines drawn from the lamp to the sample and from the sample to the detector.

The term "transilluminator" as used herein means a device (other than a fluorometer requiring placement of fluorophor-labeled sample in a specially constructed sample holder) which allows light to shine through a surface in or on which a fluorophor-containing material has been placed, and includes horizontal electrophoresis devices and other devices in which fluorescent-containing materials are distributed on a surface.

Also provided are methods for making such systems and devices incorporating the light source and filters described above for viewing patterns of fluorescences emitted by fluorophors, said method comprising:

(a) providing a light source capable of producing light in the visible spectrum;

(b) placing said fluorophors spaced apart from said light source;

(c) placing a first optical filter between said light source and said fluorophors, said filter being capable of transmitting light from said light source of the excitation type for said fluorophors and of preventing transmission of light from said light source of the emitted type for said fluorophors; and (d) placing a second optical filter between said fluorophors and a light detector, said second filter being capable of transmitting light of said emitted type and of preventing transmission of light from said light source of said excitation type.

Also provided are methods for viewing a pattern of fluorescence emitted by fluorophors capable of emitting light of an emitted type when excited by light of an excitation type different from said emitted type, at least a detectable portion of said emitted type being present in visible light, said method comprising:

(a) shining visible light on said fluorophors through a first optical filter which is capable of transmitting light of said excitation type and of preventing transmission of light of said emitted type, whereby said fluorophor emits light of said emitted type;

(b) passing light emitted by said fluorophor through a second optical filter which is capable of transmitting light of said emitted type and of absorbing light from the light source of said excitation type to form an image of said pattern of fluorescence; and (c) viewing said image.

Devices of this invention use visible rather than ultraviolet light for exciting and viewing fluorescence. Preferred embodiments of this invention using light sources of around 9 W emit even less dangerous UV light than standard fluorescent tubes used in most offices and laboratories. Using visible light allows the integrity of DNA being viewed to be maintained. The devices of this invention allow detection of as little as 0.1–1 ng of DNA, equal to or slightly better than a 312 nm UV transilluminator. Using a charge-coupled device (CCD) camera, it is possible to detect levels as low as tens of picograms of SYBR Gold-stained DNA. Viewing may be done by eye or by an imaging device such as a camera or computer scanner using both conventional photography and digital imaging systems.

BRIEF DESCRIPTION OF THE FIGURES

FIG. 13 shows a scheme for a transilluminator for viewing fluorescent materials in gels and other transparent media.

FIG. 14 shows a scheme for a top-illuminator for viewing fluorescent materials in opaque media such as thin-layer chromatography plates.

FIG. 15 shows a scheme for viewing the position of fluorescent materials during column chromatography.

FIG. 16 shows a gel electrophoresis apparatus in which the two plates containing the gel also act as the two filters, allowing fluorescent materials to be viewed during electrophoresis.

FIG. 17 shows a thin-layer chromatography apparatus in which the filters are an integral part of the apparatus, allowing fluorescent materials to be viewed during thin-layer chromatography.

FIG. 18 shows a handheld unit in combination with glasses worn by the viewer having as lenses the second optical filter.

FIG. 19 shows a transilluminator of this invention comprising a handheld second filter useful to manually scan fluorescent materials and quantitate amounts present.

DETAILED DESCRIPTION

Figure 1:
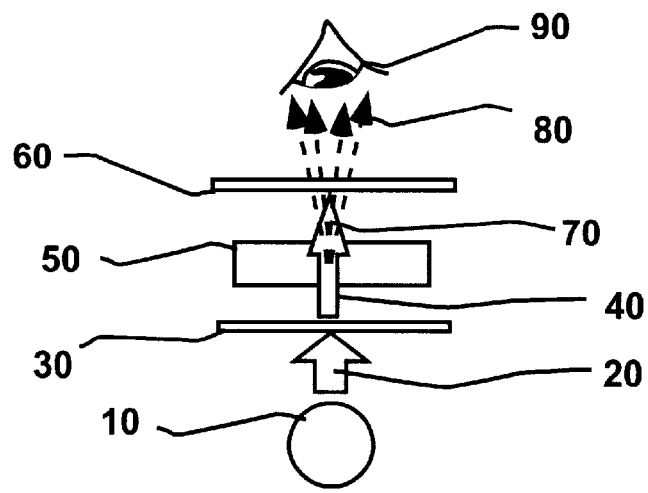
FIG. 1 is a scheme illustrating the operational principles of a device of this invention.

What the human eye perceives as "white light" consists of all the electromagnetic radiation with wavelengths between approximately 400 and 750 nm (the "visible spectrum"). (Light from 200–400 nm is called ultraviolet or UV.) Different wavelengths of light, when isolated, are seen by the human eye as being colored: light of wavelengths between 400–500 nm is generally seen as violet/blue hues; 500–550 nm is seen as green/yellow hues; and 550–750 nm is seen as orange/red hues. The term "visible light" as used herein refers to light having wavelength(s) between about 400 nm and about 750 nm. Not all wavelengths in this range need to be present in the "visible light" for purposes of this invention.

Many dyes are excited to fluoresce by light within the visible spectrum. However, prior to the present invention, this fluorescence has not been used in transilluminators or in handlamps because when white or broad-band visible light is used for excitation of the dye, the fluorescence is not detectable due to the large amount of incident light from the light source itself that reaches the observer or detecting instrument. This problem is overcome in the present invention by placing suitable optical filters on either side of the material to which the fluorophor is bound to prevent the totality of the lamp light from reaching the observer and allow the fluorescent light from the fluorophor to be seen.

"Optical filters" remove or "absorb," i.e., prevent transmission of, light of a certain type while allowing the passage or "transmittance" of light of another type. For example, a color filter that appears blue is absorbing most of the green and red light and transmitting the blue light. A color filter that appears amber is absorbing blue light and transmitting green and red light. The combination of green and red light appears yellow-orange to the eye, giving the filter a yellow-orange or amber color.

The exact optical properties of a color filter are due to the light absorption properties of the particular pigments embedded in its matrix. The filter matrix itself may be made from a wide range of materials known to the art and available to the skilled worker including plastics, such as acrylics, gelatin and glass.

Another type of optical filter is a polarizing filter. A polarizing filter transmits light of only a narrow range of orientations and prevents transmission of light of other orientations.

The optical properties of filters are measured in terms of either the "absorbance" or "percent transmittance." The terms are related as shown below:

$$A = -\log(\%T/100)$$

where A is the absorbance of the filter and %T is the percent transmittance.

"Fluorescence" is the phenomenon in which light energy ("exciting light") is absorbed by a molecule resulting in the molecule becoming "excited." (Lakowicz, J. R. (1983) "Principles of Fluorescence Spectroscopy," Plenum Press, N.Y.) After a very brief interval, the absorbed light energy is emitted by the excited molecule, usually at a longer wavelength than the exciting light. This emitted light is referred to as fluorescent light. A molecule that exhibits fluorescence is referred to as a "fluorophor."

Any given fluorophor will be excited to fluoresce more by some wavelengths of light than other wavelengths. The relationship between wavelengths of light and degree of excitation of a given fluorophor at that wavelength is described by the "excitation spectrum" of the fluorophor. The excitation spectrum is also called the "excitation wavelength range" herein.

Figure 2:
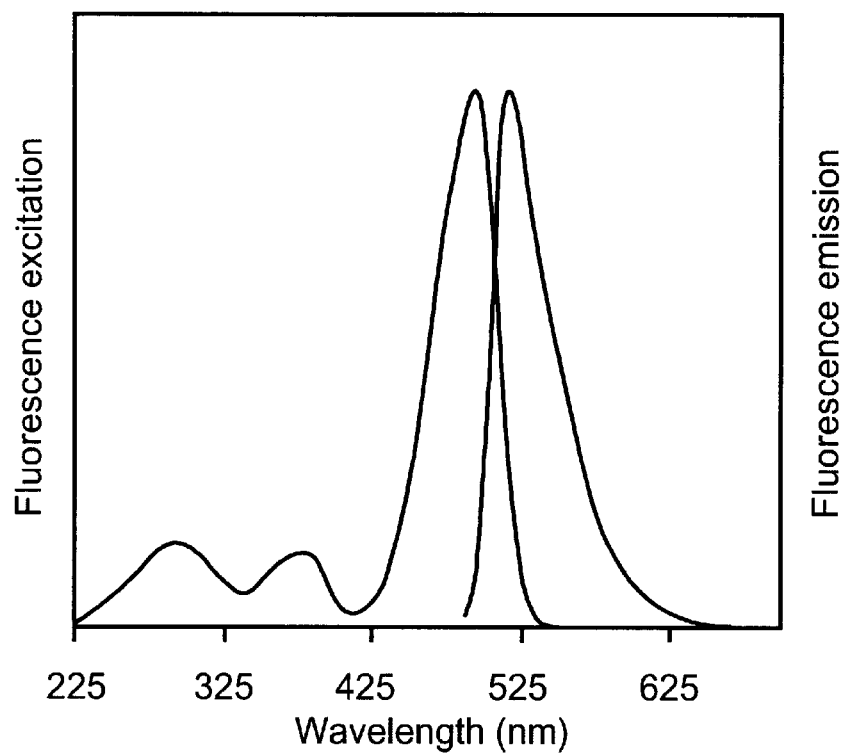
FIG. 2 is a graph showing the fluorescence excitation and emission spectra of a double-stranded DNA-bound SYBR Green I nucleic acid gel stain.

Likewise, any given fluorophor will produce more intense fluorescence at particular wavelengths than others. The exact relationship between the wavelength of light and the intensity of the fluorescence emission at that wavelength is described by the "emission spectrum" or "fluorescence spectrum" of the fluorophor. The emission spectrum is also called the "emitted wavelength range" herein. FIG. 2 graphs the fluorescence excitation and emission spectra of a double-stranded DNA-bound SYBR Green I nucleic acid gel stain as taken from R. Haugland (1996) "Handbook of Fluorescent Probes and Research Chemicals."

The excitation maximum is the wavelength of exciting light at which fluorescence of the fluorophor reaches maximum intensity. The emission maximum is the wavelength of light emitted by the excited fluorophor when its fluorescence is at maximum intensity.

Most fluorophors excited by and emitting visible light have an emission spectrum overlapping their excitation spectrum, although the maximum for each is different. The distance in nanometers between the excitation spectrum maximum and the emission spectrum maximum is known as the "Stokes' shift." Fluorophors with large Stokes' shifts in the visible range work best in this invention. For example, a fluorophor with an excitation maximum of 450 nm and an emission maximum of 600 nm with no overlapping between the spectra would be ideal; however most fluorophors have smaller Stokes' shifts. For example, SYPRO Orange has a Stokes' shift of 105 nm and SYPRO Gold has a Stokes' shift of 42 nm, while fluorescein has a Stokes' shift of 25 nm.

Figure 3:
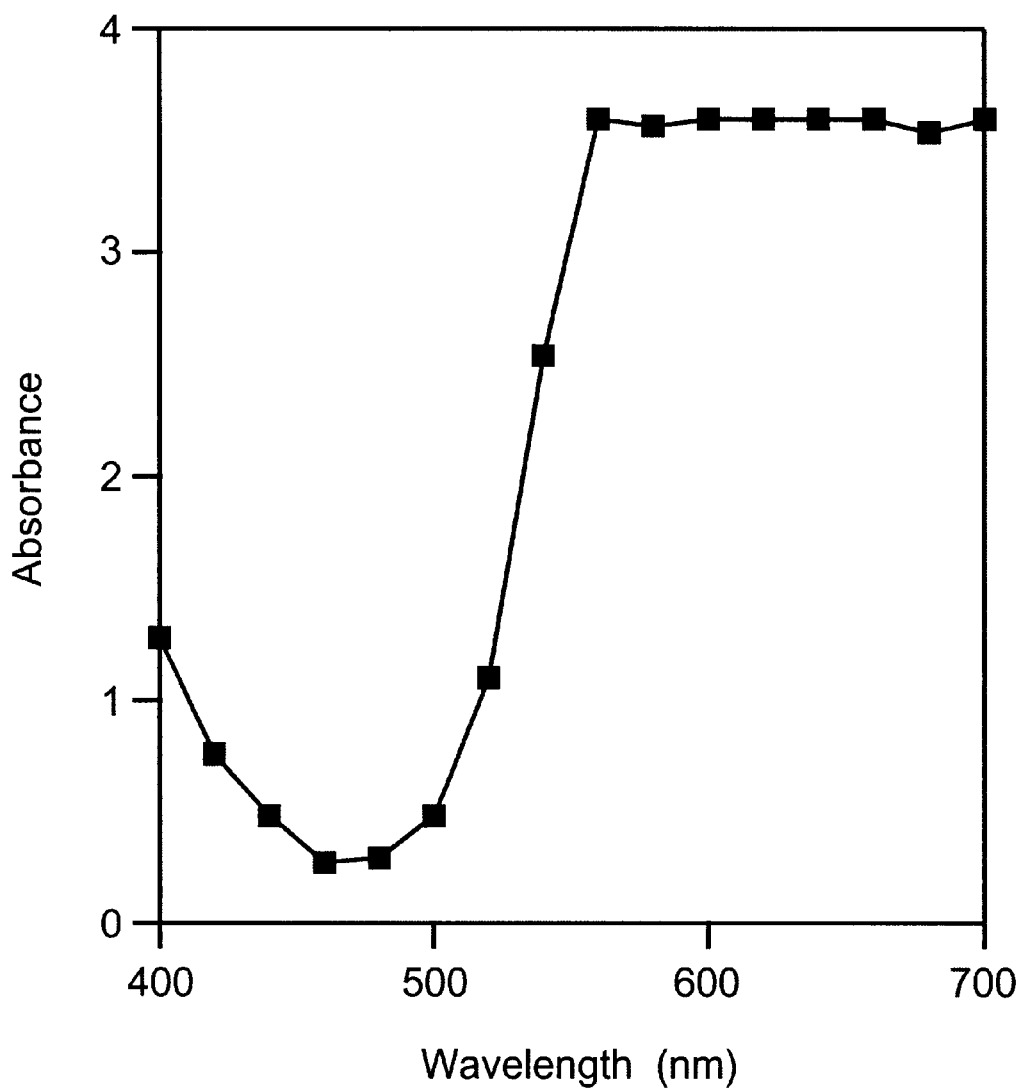
FIG. 3 shows the absorbance spectrum of the Acrylite #668-0GP optical filter used as a first optical filter in a preferred embodiment of this invention.
Figure 4:
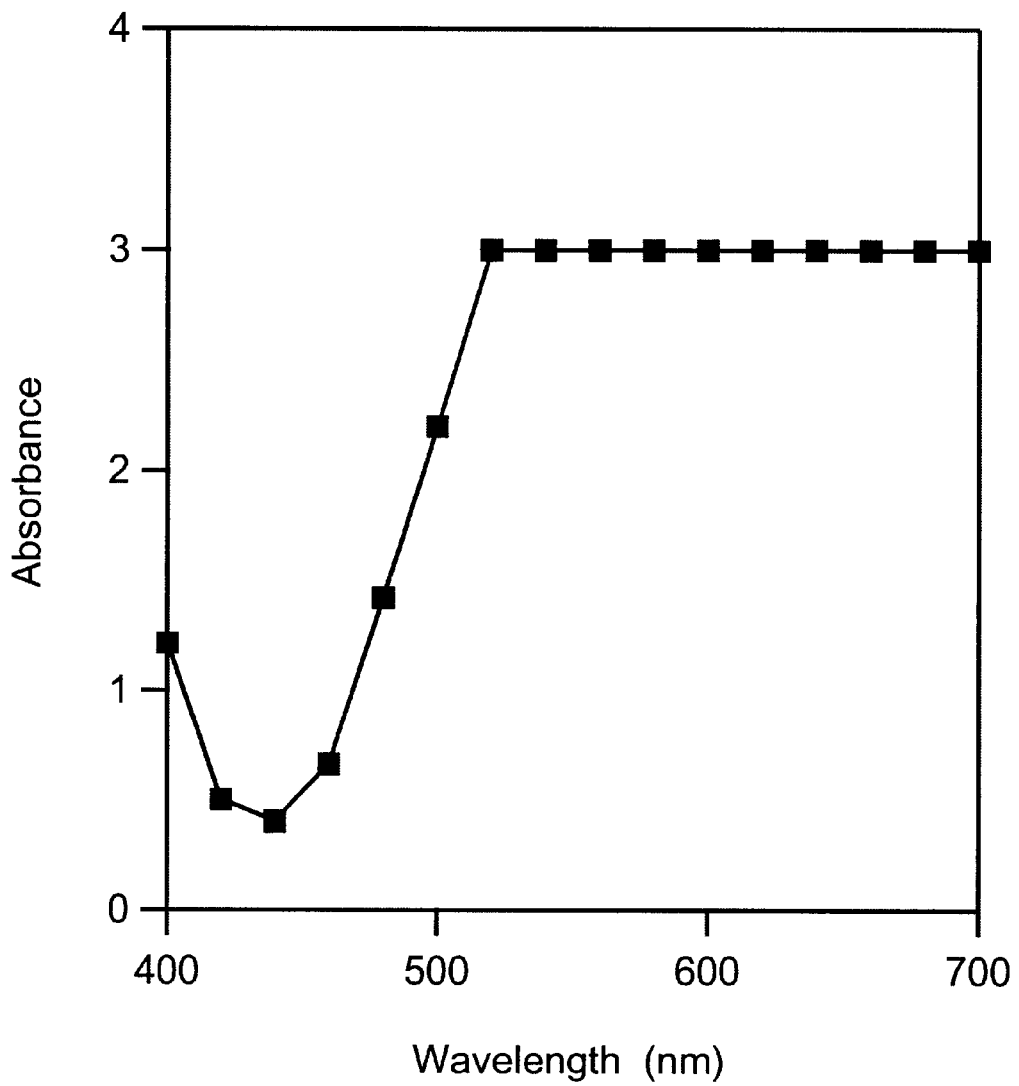
FIG. 4 shows the absorbance spectrum of the Wratten #98 optical filter used as a first optical filter in a preferred embodiment of this invention.

Visible light sources of this invention typically emit light which includes or overlaps both spectra. Most color filters do not sharply transmit light only within a certain wavelength, and sharply prevent transmission of all light outside this wavelength. Instead, as shown in FIGS. 3 and 4, most filters allow passage of a small quantity of light even at wavelengths where they are most effective as filters, and they prevent transmittance of a small quantity of light at wavelengths where they are least effective as filters for absorbing light. In a "crossover" wavelength range, the capability of such color filters to absorb light changes (gradually or sharply) along the wavelength scale from a region where maximum light is being absorbed, known as the "cut-off region," to a region where most of the light is being transmitted and only a small amount is being absorbed. As a practical matter, the light source will produce light in wavelengths overlapping those emitted by the fluorophor, and the filter between the fluorophor and the viewer used to transmit light in the emission spectrum will also allow enough light from the source to pass through to overwhelm the fluorescence (emitted spectrum). Thus a filter placed between the light source and the fluorophor to remove light from the source not removed by the filter between the fluorophor and the viewer must be used. To optimize the sensitivity of the system, filter pairs should be chosen so as to allow viewing of (a) the maximum fluorescence intensity and (b) minimum lamp light intensity. For typical fluorophors this involves a tradeoff between (a) and (b). The system can be adjusted to minimize lamp light intensity so that the lamp light does not overpower the fluorescence.

A first consideration is to choose the filter pairs so that in combination they prevent transmission of essentially all the exciting light to the viewer. To achieve this, assuming the lamp produces light as close to the excitation maximum of the fluorophor as possible: (a) the first filter must absorb as much light as possible in the emission spectrum of the fluorophor, i.e., in general the cut-off region must extend as far into the blue (shorter wavelengths) as practicable; and (b) the second filter must absorb as much light as possible in the excitation spectrum of the fluorophor, i.e., the cut-off region must extend as far into the red (longer wavelengths) as practicable. This tends to result in the use of filters whose crossover regions are far apart and not overlapping.

A second consideration for choosing the filter pairs is to maximize the amount of light in the emission spectrum for the fluorophor that reaches the viewer: (a) the first filter should be selected to transmit as much light as possible in the region of excitation maximum of the fluorophor; and (b) the second filter should be selected to transmit as much light as possible in the region of the emission maximum of the fluorophor. This tends to result in the use of filters whose crossover regions overlap. The point along the wavelength range where the absorbances of the two filters coincide should be at as high an absorbency as practicable.

If the maximum of the emission spectrum for a fluorophor is greater than 500 nm, the absorbance of the filter selected to be placed between the fluorophor and the light source may rise to near 4 from less than 1 in a crossover region, e.g., from about 450 nm to about 500 nm. (Good filters have a crossover region of less than about 50 nm.) The absorbance of the second filter between the fluorophor and the viewer should then drop from near 4 to less than 1 in the same crossover region such that the sum of the absorbances of the filters at wavelengths in the crossover region is near 4 to filter out most of the wavelengths in this region so that light below about 525 nm is effectively prevented from reaching the viewer. Thus the viewer sees substantially only light emitted by the fluorophor.

As discussed above, the excitation and emitted wavelength ranges of the fluorophor can overlap. The only requirement is that light of sufficient intensity to be detectable in a darkened space (preferably by the viewer's unaided eye but alternatively by an optical instrument such as a camera or optical scanner) be emitted by the fluorophor outside the excitation wavelength range so that it can be detected after light in the excitation wavelength range has been filtered out.

Typical fluorophors include many organic dyes. However, most molecules of biological origin such as nucleic acids, proteins, lipids and coenzymes are not strongly fluorescent. (Notable exceptions include Green Fluorescent Protein and its derivatives and various pigments such as chlorophyll and others used for coloration of plants and animals.) Therefore, to detect biological molecules it is usually necessary to either stain or react a biological sample with a fluorophor. "Staining" usually refers to the process in which a fluorescent dye binds relatively weakly to a target molecule without the formation of covalent bonds. If a fluorophor is "reacted" with a target molecule, this usually implies that the complex between the two species involves a relatively robust covalent bond.

The fluorescence intensity of a sample can be used either qualitatively to determine the presence or location of a fluorophor or quantitatively to determine the amount of fluorophor present. Variants on measuring the intensity of fluorescence include fluorescence resonance energy transfer and fluorescence polarization.

Alternatively, a fluorophor may be used indirectly to reveal the presence of a particular species. For example, the Vistra ECF Substrate system (Amersham Life Science Inc., Arlington Heights, Ill.) involves the use of the enzyme alkaline phosphatase, conjugated to an antibody that can bind specially prepared DNA oligonucleotide probes, to generate a fluorescent species. The enzymatic reaction generates multiple fluorophors, effectively providing an "amplified" fluorescence signal from the target DNA.

Some examples of fluorophors used with biological samples are given in Table 1.

The removal of lamp light by filters so that the viewer sees substantially only the light emitted by the fluorophor is accomplished in two steps (see FIG. 1). In a preferred embodiment, a filter pair comprising a blue first filter and an amber second filter is used with a fluorophor such as SYBR® Green I or ethidium bromide that is maximally excited at around 500 nm or less (i.e., by blue light) and emits its maximum fluorescence at 500 nm or more (i.e., the fluorescence is green or red).

The first filter, which is blue, is placed between the light source and the fluorophor and absorbs the green and red components of the visible light and transmits only blue light through to the fluorophor. The blue light excites the fluorophor to fluoresce. Between the fluorophor and observer is placed a second filter, which is amber, that absorbs the blue light from the lamp but transmits the green or red fluorescent light from the fluorophor to the light detector, e.g., a human viewer or detection equipment.

Another embodiment uses polarizing filters. For a typical light source the light is polarized equally around all possible orientations. By placing a polarizing filter in front of a lamp it is possible to select light with a narrow range of orientations. If a second polarizing filter is placed on top of the first filter but orthogonal to the first, then this second filter will remove essentially all of the polarized light that has passed through the first filter. The net result is that no light reaches the viewer. When a fluorescent sample is placed on top of the first filter, the some of the sample will be excited by the polarized light that passes through the first filter. The sample will emit fluorescence. This fluorescence is also polarized. However, the emitted light will have a fairly broad distribution of orientations. Some of these orientations will be able to pass through the second filter and reach the viewer. The net result is that the fluorescence can be seen by the viewer against a dark background.

The "light source" used in this invention is any device capable of emitting visible light e.g., a typical household light such as a low-powered fluorescent tube or incandescent bulb that produces visible light including wavelengths within the excitation spectrum of the fluorophor. Different lamps produce different intensities of light at different wavelengths. Thus, for example, by altering the phosphor in a fluorescent tube, a lamp that will have maximum light output at wavelengths where excitation of the fluorophor is maxi-

TABLE 1

| Dye | Excitation Maximum (nm) | Emission Maximum (nm | Uses |
|---|---|---|---|
| ethidium bromide (EB)[1] | 518 | 605 | stain for nucleic acids |
| SYBR ® Green[2] | 494 | 521 | stain for nucleic acids |
| SYPRO ® Orange[5] | 485 | 590 | stain for proteins |
| SYBR ® Gold[2] | 495 | 537 | stain for nucleic acids |
| GelStar ®[3] | 493 | 527 | stain for nucleic acids |
| Vistra ™ Green[4] | 497 | 520 | stain for nucleic acids |
| Vistra ™ ECF Substrate[4] | 440 | 560 | indirect detection |
| 4-chloro-7-nitrobenz-2-oxa-1,3-diazol[1] | 467 | 539 | covalent label |
| fluorescein derivatives[1] | 495 | 520 | covalent label |
| Texas Red ®[2] | 587 | 602 | covalent label |

[1]Available from Sigma Chemical Co., St. Louis, MO.
[2]Trademark of Molecular Probes, Inc. of Eugene, OR.
[3]Available from FMC Bioproducts, Rockland, ME.
[4]Available from Amerisham Life Science Inc., Arlington Heights, IL.
[5]SYPRO ® is a trademark of Molecular Probes, Inc. of Eugene, OR.

mal may be manufactured. Some examples are given in Table 2.

TABLE 2

| Lamp | Maximum Output (nm) | Half width of Output (nm) | Relative Output at Maximum |
|---|---|---|---|
| Phillips F40B[1] | 460 | 160 | 0.19 |
| Interelectric F40T12/BBY[2] | 445 | 33 | 1.00 |
| Nichia NP-160[3] | 480 | 120 | 0.35 |
| Panasonic FPL28EB[4] | blue | | |
| Panasonic FML27EB[4] | blue | | |
| Sylvania CF9DS/blue[5] | 457 | 46 | |
| Dulux S9W F9TT/Green[6] | 550* | 25 | |
| Dulux S9W F9TT/Red[6] | red | | |

[1]Available from Phillips Lighting Co. of Somerset, NJ.
[2]Available from Interelectric Corporation, Warren, NJ.
[3]Available from Nichia America Corporation of Mountville, PA.
[4]Available from Matsushita Home and Commercial Products Company, Secaucus, NJ.
[5]Available from Osram Sylvania, Inc., Maybrook, NY.
[6]Available from Osram Corporation, Montgomery, NY
*Main peak.

The first optical filter is placed between the fluorophor and the light source and transmits light from the light source in the wavelength range of the excitation spectrum of the fluorophor. As most fluorophors useful with the invention are maximally excited between about 450 nm and 550 nm, the first optical filter will typically appear blue or green to the eye.

It is essential the first optical filter also prevent the transmittance of (absorb) as much light as possible from the light source that is of similar wavelengths to the fluorescence emission of the fluorophor. A filter with a percent transmittance of around 0.01% at wavelengths in the emission spectrum of the fluorophor is desirable.

Examples of filters with these properties include Acrylite® #668-0GP, available from Cyro Industries of Rockaway, N.J. and Wratten #98, made by Eastman Kodak Company of Rochester, N.Y. FIG. 3 shows the absorbance spectrum of this Acrylite #668-0GP filter measured by an instrument capable of measuring absorbances up to 3.5. FIG. 4 shows the absorbance spectrum of the Wratten #98 filter from the Kodak Photographic Filters Handbook. The data set does not extend above absorbances of 3.0.

The second optical filter should transmit only light with wavelengths in the region of the fluorescence emission spectrum of the fluorophor. As most fluorophors useful with the invention have emission spectra between about 500 nm and about 650 nm, the second filter will typically appear yellow, amber or red to the eye.

Figure 5:
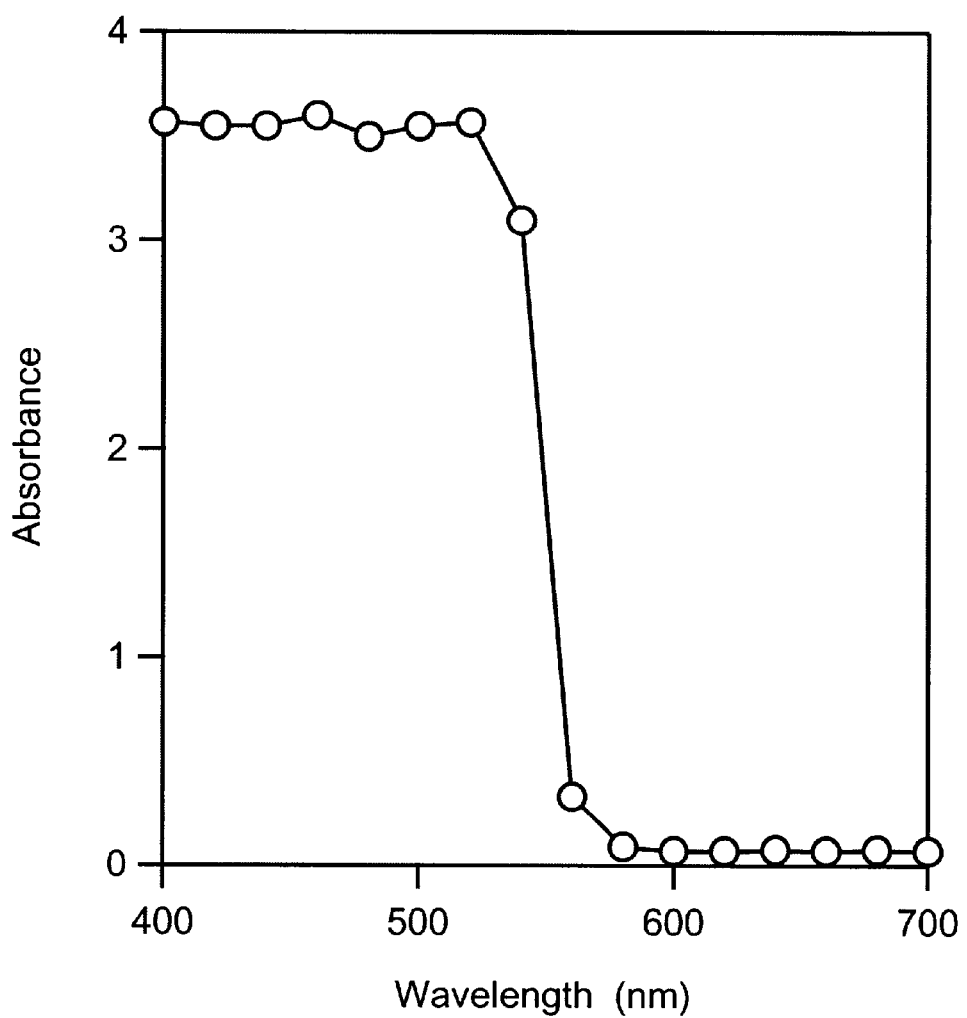
FIG. 5 shows the absorbance spectrum of the Perspex #300 optical filter used as a second optical filter in a preferred embodiment of this invention.
Figure 6:
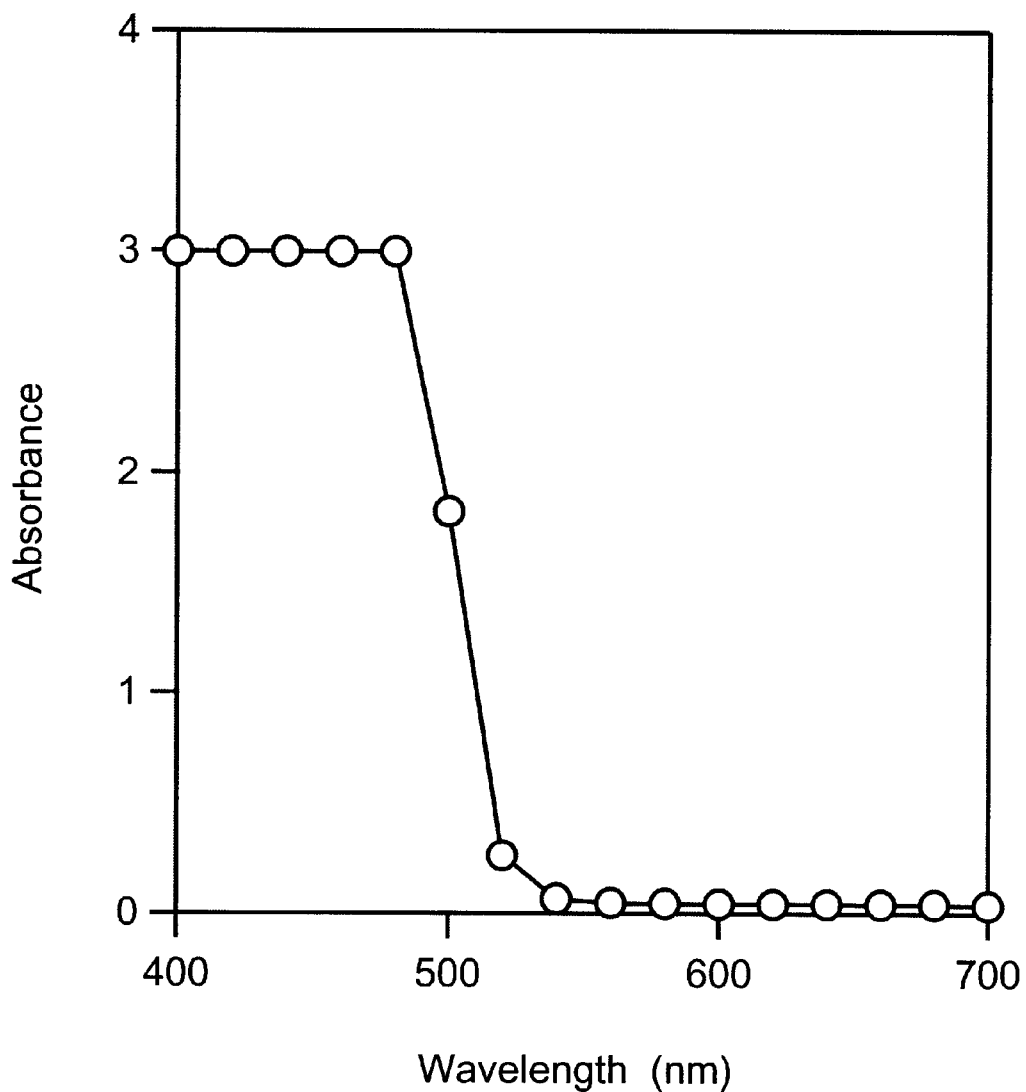
FIG. 6 shows the absorbance spectrum of the Wratten #12 optical filter used as a second optical filter in a preferred embodiment of this invention.

It is essential the second filter effectively prevent the transmittance of as much light as possible from the lamp that is transmitted by the first filter. For most fluorophors described herein, this means the second filter must absorb blue light. A filter with a percent transmittance of less than 0.1% in the blue region is desirable. Filters with these properties include Perspex® #300 made by ICI Chemicals and Polymers Limited of Darwen, Lancs., U.K. and Wratten #12 made by Eastman Kodak Company of Rochester, N.Y. FIG. 5 shows the absorbance spectrum of the Perspex® #300 filter measured by an instrument capable of measuring absorbances up to 3.5. FIG. 6 shows the absorbance spectrum of the Wratten #12 filter from the Kodak Photographic Filters Handbook. The data set does not extend above absorbances of 3.0. The Acrylite #408-5GP filter made by Cyro Industries of Rockaway, N.J., even though it has acceptable transmittance properties, should not be used alone due to intrinsic fluorescence.

In some cases, the use of two amber filters together may be desirable. For example, the combination of Wratten #12 with Lee #15, made by Lee Filters, Ltd. of Andover, Hampshire, U.K. can result in enhanced levels of fluorescence detection due to a decrease of the background light transmitted. In a somewhat different situation, the Acrylite #408-5GP filter, which possesses intrinsic fluorescence, can be used if a Lee #21 filter is placed between the #408 filter and the specimen. This effectively reduces the intrinsic fluorescence. Problems caused by intrinsic fluorescence of the filter may be alleviated by moving the filter farther away from the light source.

The transmittance properties of the two filters should cross over from high to low transmittance in the case of the blue filter and low to high in the case of the amber filter, as discussed above, in such a fashion that, in combination, the two filters prevent the transmittance of lamp light to the viewer.

Figure 7:
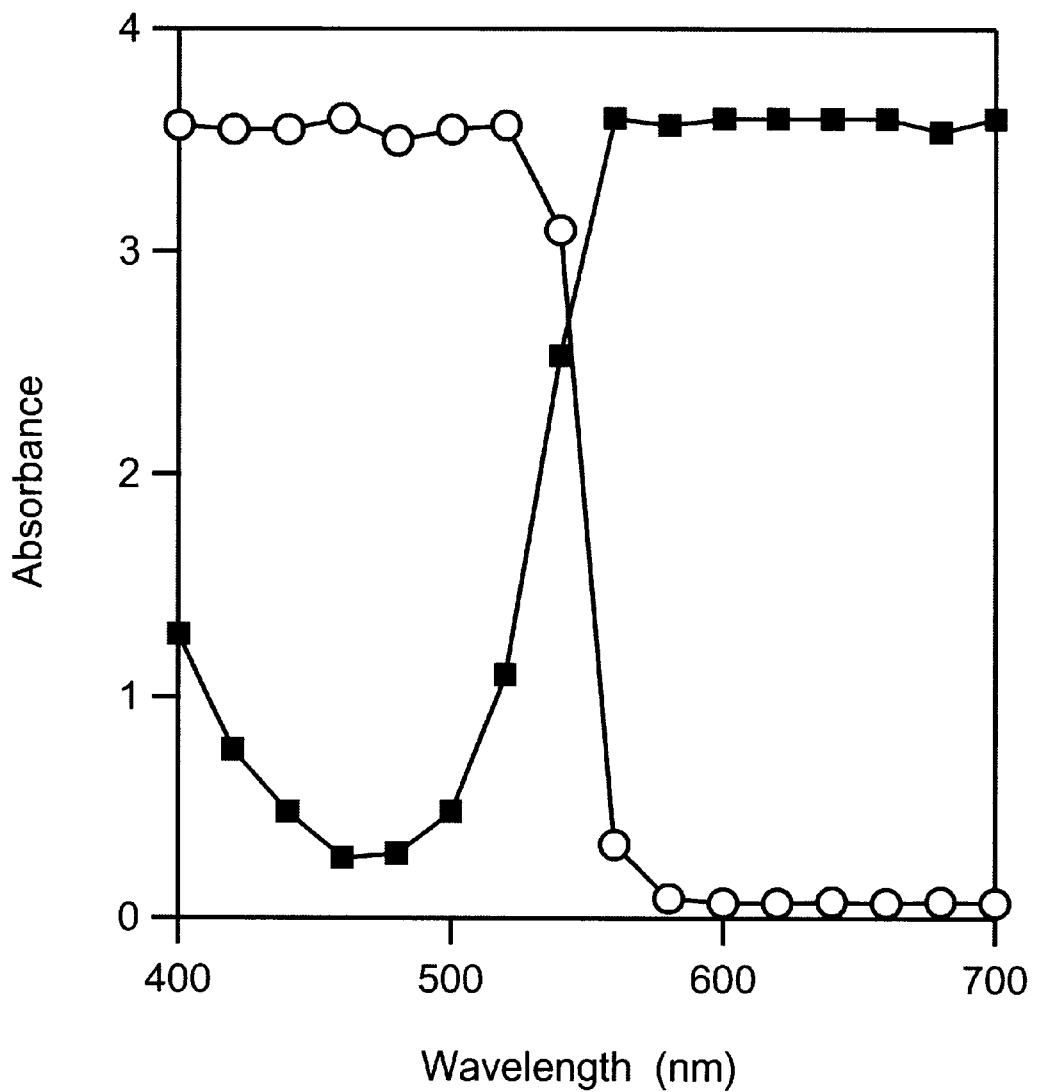
FIG. 7 shows absorbance spectra of the Acrylite #668-0GP and Perspex #300 optical filters used as a combination of first and second filters in a preferred embodiment of this invention.
Figure 8:
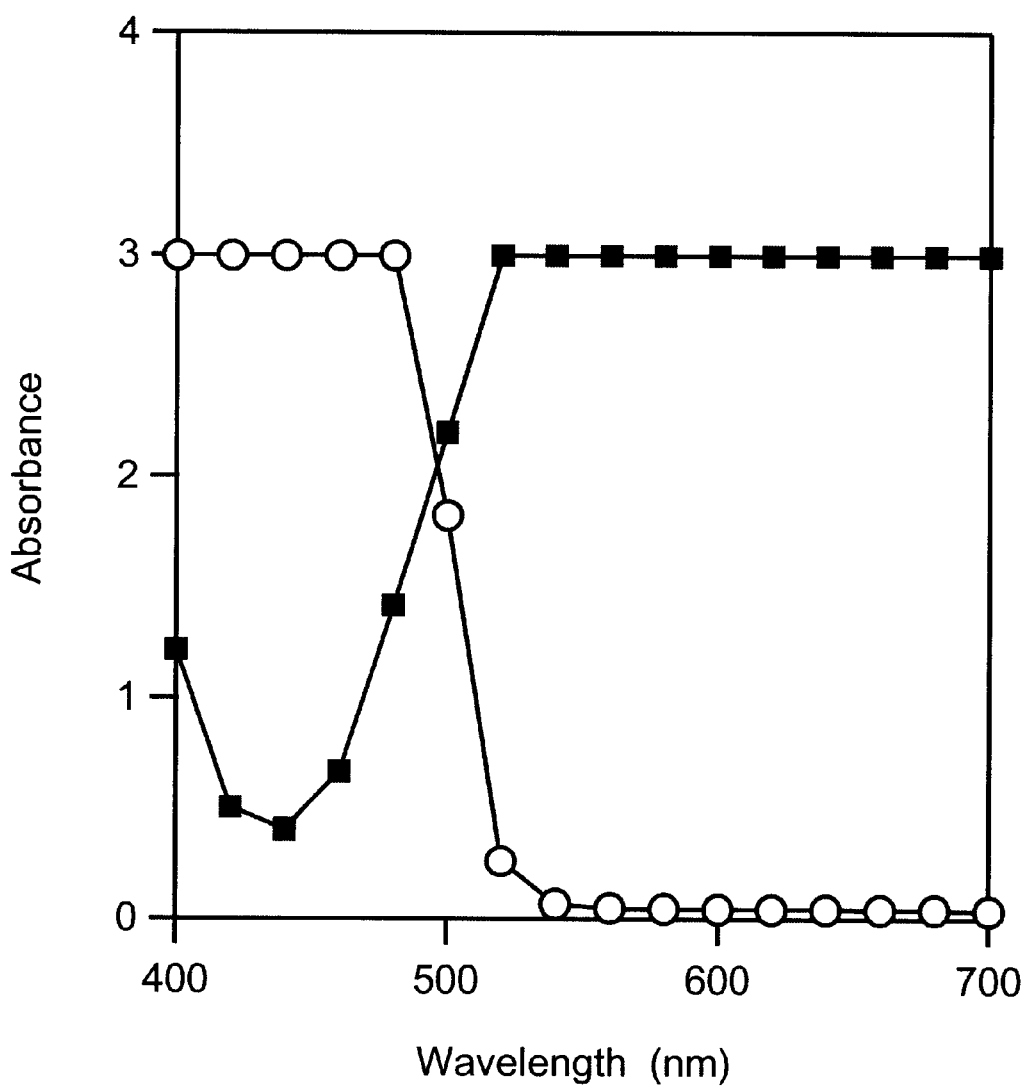
FIG. 8 shows absorbance spectra of the Wratten #98 and Wratten #12 optical filters used as a combination of first and second filters in a preferred embodiment of this invention.

Examples of useful filter combinations for this invention include Acrylite #668-0GP with Perspex® #300 (FIG. 7) and Wratten #98 with Wratten #12 (FIG. 8).

FIG. 1 is a scheme illustrating the operational principles and devices of this invention and is described with respect to preferred embodiments. A light source 10 such as a fluorescent lamp, shines broad-band visible light 20 indicated by the broad arrow onto a first optical filter 30 which removes wavelengths which do not activate fluorescent emission of the fluorophor contained on the fluorophor-containing material 50, which is typically a gel containing stained biological material. In a preferred embodiment, first filter 30 removes red and green light. After passing through filter 30, broad-band visible light 20 becomes light almost exclusively in the exciting wavelength range 40, in the preferred embodiment, blue light, indicated by the long, narrow arrow, some of which light passes through the fluorophor-containing material 50 and some of which strikes the fluorophor thereon causing it to emit light in the emission wavelength range which is mixed with a large excess of light in the exciting wavelength range to form mixed light 70, in the preferred embodiment, red or green light mixed with blue light. Mixed light 70 passes through second optical filter 60 where light in the exciting wavelength range (blue light) is removed leaving light in the emitting wavelength 80, in the preferred embodiment, red or green light, remaining to strike the light detector 90 which may be a human eye or a device such as an optical scanner or camera. In a preferred embodiment, light source 10 is contained within a light box 15 (see FIGS. 9–12), such as a conventional, commercially available visible light transilluminator. The light source 10 is preferably a fluorescent tube lamp or lamps of standard design, for example FPL28EB available from Matsushita Home and Commercial Products Company of Secaucus, N.J. or CF9DS/blue available from Osram Sylvania, Inc., Maybrook, N.Y. The sensitivity of the device may be enhanced by using lamps that provide the maximum light output in the region of the exciting light spectrum (between 450 and 500 nm in the preferred embodiment). First filter 30 is preferably a piece of semi-transparent material attached to the top of the light box 15 of sufficient size to cover the entire surface of the transilluminator. The optical properties of the sheet in the preferred embodiment are such as to allow through light of less than about 500–550 nm and cut off light of longer wavelengths. Any type of film or screen with these optical properties may be used. A preferred embodiment uses an Acrylite #668-0GP filter. The fluorophor-containing material 50 is preferably a fluorescently stained DNA gel. Second optical filter 60 may be in the form of a sheet directly over the gel or attached to an imaging device or in the form of lenses for glasses 28 (shown in FIG. 18). This filter 60 is a semi-transparent film or sheet that cuts off light of wavelengths less than the emitting wavelength range, or at least the emitting wavelength maximum, i.e., less than about 500–550 nm in the preferred embodiment, and allows through light of longer wavelengths. Any type of film or screen with these optical properties may be used. A preferred embodiment uses the Perspex® #300 filter. When the second filter 60 is a sheet, it is placed on top of the gel in the preferred embodiment, and is supported along the edges to avoid contact with the gel. This filter 60 may be attached to the light box by a hinge or other device known to the art if desired.

The light source can be of many types and incorporated into many structures. Any suitable source of light capable of illuminating the entire sample in the exciting wavelength range for the fluorophor being used may be employed as light source 10, for example a TV screen, photocopier, overhead projector, slide projector, camera flash, street light, strobe light, car headlight, computer scanner, or light-emitting diode may be used.

The systems of this invention may be used for both quantitative and qualitative analysis, detection, imaging, spectroscopy, chromatography, microscopy, DNA sequencing, cloning, polymerase chain reaction (PCR) processes, cell sorting, repair of DNA damage or mutation, e.g. due to aging or cancer, live animal studies, e.g., genetically altered mice containing the gene for green fluorescent protein, and the like, bacterial identification, detection and growth monitoring, medical diagnosis, e.g., detection of fungal infections on skin, industrial and environmental studies, mineral studies, and hobbies, e.g., the enjoyment of tropical fish and other tropical marine species that naturally contain fluorescent pigments.

In a preferred embodiment, an agarose or polyacrylamide gel in which DNA fragments have been previously separated by electrophoresis is stained with a suitable fluorescent dye such as ethidium bromide as described in a standard manual of laboratory techniques in molecular biology, or in the case of SYBR Green I and SYBR Gold, as described in the literature provided by Molecular Probes, Inc. of Eugene, Oreg. The stained gel, referred to herein as the fluorophor-containing material 50, is placed on top of (in front of with respect to the viewer) first optical filter 30. The lamps or light sources 10 in the transilluminator are switched on. Either second optical filter 60 is placed over (in front of as defined by the viewer) the fluorophor-containing material 50, i.e., the gel, or glasses 28 as shown in FIG. 18, are put on by the human viewer. Alternatively lenses designed to attach to an optical scanner or camera used as a viewer may embody second optical filter 60.

Figure 9:
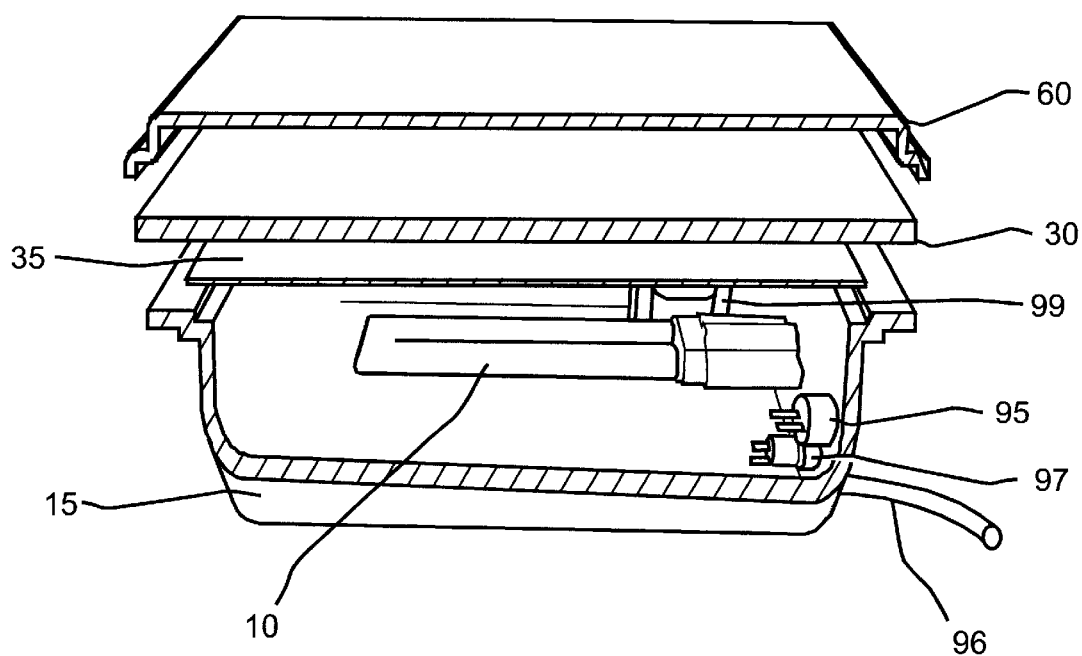
FIG. 9 is a cutaway and exploded view of a transilluminator device of this invention.

FIG. 9 is a cutaway view of a transilluminator device of this invention. Light box 15 contains electrical components, supports acrylic sheets and directs light as evenly and intensely out of the top as possible. The inside of the box is preferably made of a white plastic to reflect as much light as possible. The box preferably has curved edges and a reflector under the lamp to aid reflection. The sides are angled to aid light reflection. It is also substantially watertight and light-tight. Second optical filter 60 is preferably an amber screen comprised of 5 mm thickness Perspex®#300 acrylic which is designed to fit snugly over the top of the box and to drop down over the edge of first optical filter 30, which is preferably a blue screen. The overlap of second optical filter 60 over the edges of first optical filter 30 prevents light leakage and prevents second optical filter 60 from slipping off. For viewing by eye, the amber screen can be replaced by a pair of glasses with amber lenses. For viewing by instrument, the amber screen can be replaced by a small filter over the viewing instrument aperture. Other materials useful for the amber screen include 0.76 cm (0.3 in.) VSA orange vinyl from Northwest Laminating Company, Inc., of Seattle, Wash. and Wratten filter #21 from Eastman Kodak Co., Rochester, N.Y. The blue screen is preferably constructed from 0.635 cm (0.25 in.) Cyro Industries 668-0GP acrylic, Rockaway, N.J. It is preferably attached to light box 15 in such a way that its top surface is free of joins, holes, screws, and the like to prevent corrosion by liquids. The screen may additionally be hardened to prevent scratching. It may also be hinged so that the transilluminator can be used as a white light transilluminator if desired. To be used in daylight or lit space, the transilluminator is equipped with a viewing box, i.e., a cover over the transilluminator through the top of which the samples can be viewed.

In a preferred embodiment, beneath the first optical filter, resting on a lip provided by flaring the vertical sides of the light box, is a diffuser screen 35 to provide as intense and even a light as possible across the surface area of first optical filter 30. Preferably, the diffuser screen 35 is made of 0.16 cm (0.063 in.) white acrylic. Within light box 15 is disposed on/off switch 95, mains cable 96, and fuse 97. The device may be designed for AC or DC current. AC Ballast 99 is a magnetic ballast for the AC version of the lamp. Light source 10 may be a single 9 W, 16.5 cm (6.5 in.) blue compact fluorescent lamp CF9DS/blue from Osram/Sylvania, Inc., Maybrook, N.Y., attached to a vertical area of the back wall and centrally located to ensure even light distribution. A larger version of the transilluminator contains two 28 W fluorescent lamps (FDL28EB) available from Matsushita Home and Commercial Company, Secaucus, N.J.

Figure 10:
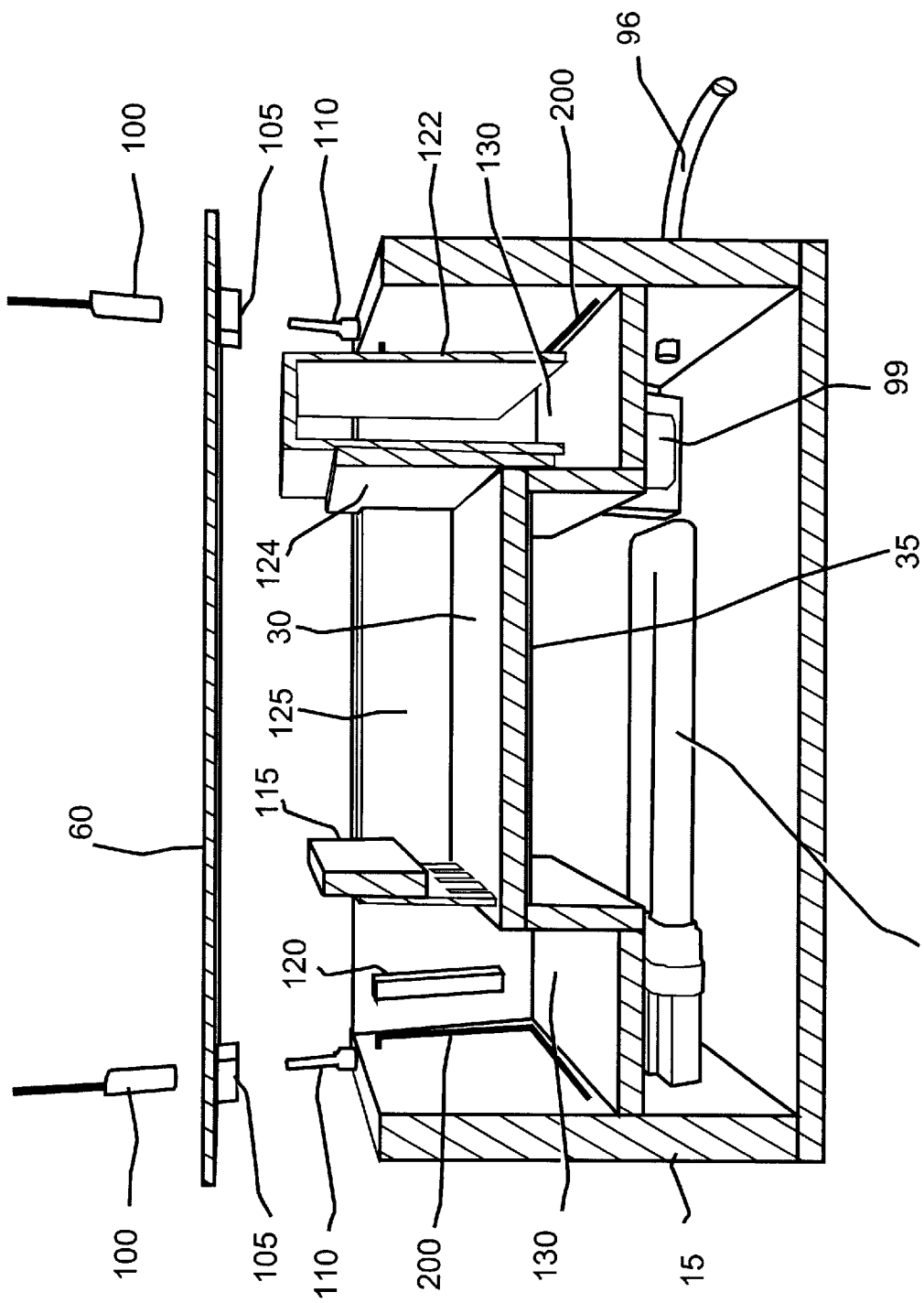
FIG. 10 is a cutaway view of an integrated transilluminator and horizontal electrophoresis unit of this invention.

FIG. 10 is a cutaway view of an integrated transilluminator and horizontal electrophoresis unit of this invention. The unit comprises female connectors 100 from a DC power supply (not shown), designed to mate with male connectors 110 placed behind or through second filter 60 which is separated from the main portion of light box 15 by blocks 105. The DC power supply via platinum electrode 200 supplies voltage across a gel to fractionate a DNA sample. The second filter also serves as a safety lid. First filter 30 also serves as a bed for the agarose gel which acts as fluorophor-containing medium 50. Dam support strips 120 and dam support panel 125 support dam spring 122 which is made of spring-loaded plastic and squeezed to fit between dam support 120 and first filter support. Teflon-coated foam 124 is attached to dam spring 122 so that it is forced against the gel support to form a water-tight seal. A similar dam (not shown) is placed on the right side of the device. The dams are used to contain the liquid agarose as it gels. Comb 115 functions to provide wells in the agarose gel into which samples may be loaded. Diffuser 35 is disposed between first filter 30 and light source 10 to spread the light evenly. Reservoirs 130 hold buffer. Ballast 99 for the light source is disposed beneath one of the reservoirs 130, connectable to an AC power supply via mains cable 96. Alternatively, the light source may be powered from a DC source.

In operation, a DNA sample is incubated with SYBR Green I diluted 100-or 1000-fold in TAE, loading buffer is added and then the sample is loaded into a well in the agarose gel. The sample is then electrophoresed at around 100 V and 50 mA. The light source is switched on. DNA fragments are viewed as they separate. Once a DNA band of interest is separated from the rest of the mixture, the electrophoresis can be stopped and the gel photographed and the band cut out if desired. For simple mixtures, different DNA bands become separated in minutes. Thus the device dramatically reduces standard "blind" UV electrophoresis time of about two hours. DNA samples can also be prestained, such as with ethidium bromide, and viewed as they fractionate.

Figure 11:
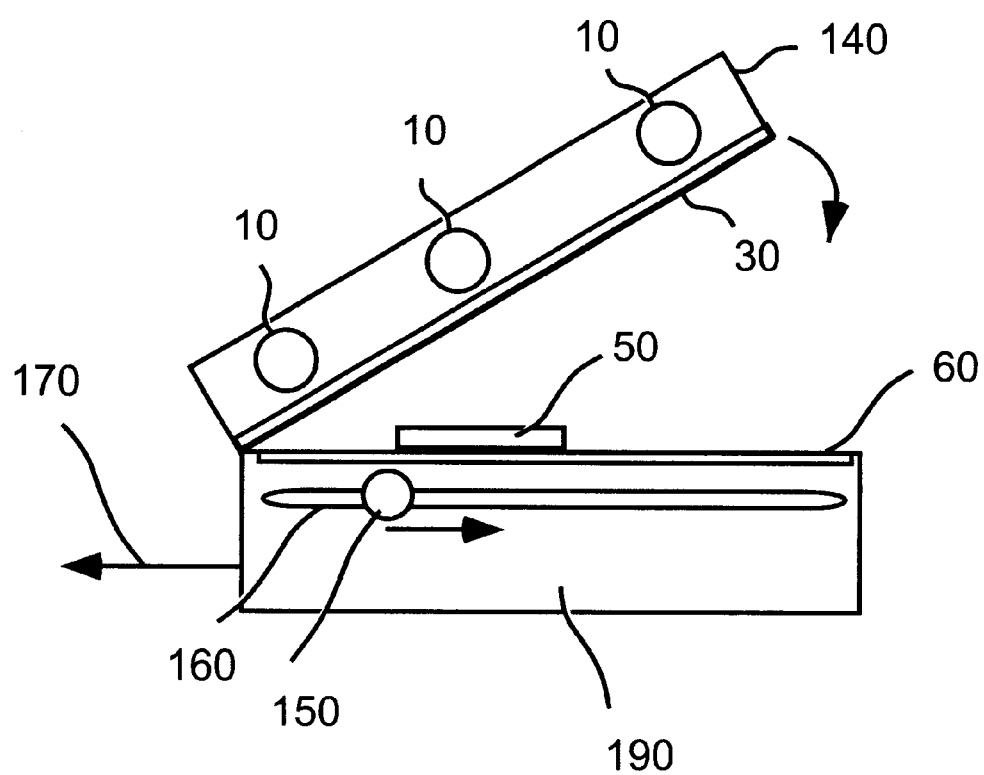
FIG. 11 is a side view of an integrated scanner-transilluminator device of this invention.

FIG. 11 shows a side view of an integrated scanner-transilluminator device of this invention using a modified commercially available scanner. Light sources 10 are contained within lid 140, as is first filter 30. This lid may be used to replace the standard transparency attachment on many scanners. Lid 140 is preferably rotatably connected, e.g. by means of hinges (not shown) to the photodetector container 190, the top surface of which comprises second filter 60 designed so the gel is not squashed when the lid 140 is lowered. Photodetectors 150 disposed within container 190 move on a track 160 or are moved by other means known to the art to scan a fluorophor-containing material 50 placed atop second filter 60. Photodetector container 190 also comprises means for detecting the fluorescent light, digitizing the scanned image (not shown) such as a processor comprising scanner software (not shown) known to the art, and digitalized image data 170 is sent to a computer (not shown) for analysis. Sensitivity of most commercially available scanners should be improved about 40-fold, e.g. by slowing the scan speed of the photodetectors 150, or by replacing the photo diode array with more sensitive means such as a charge-coupled device, for use in this invention.

Figure 12:
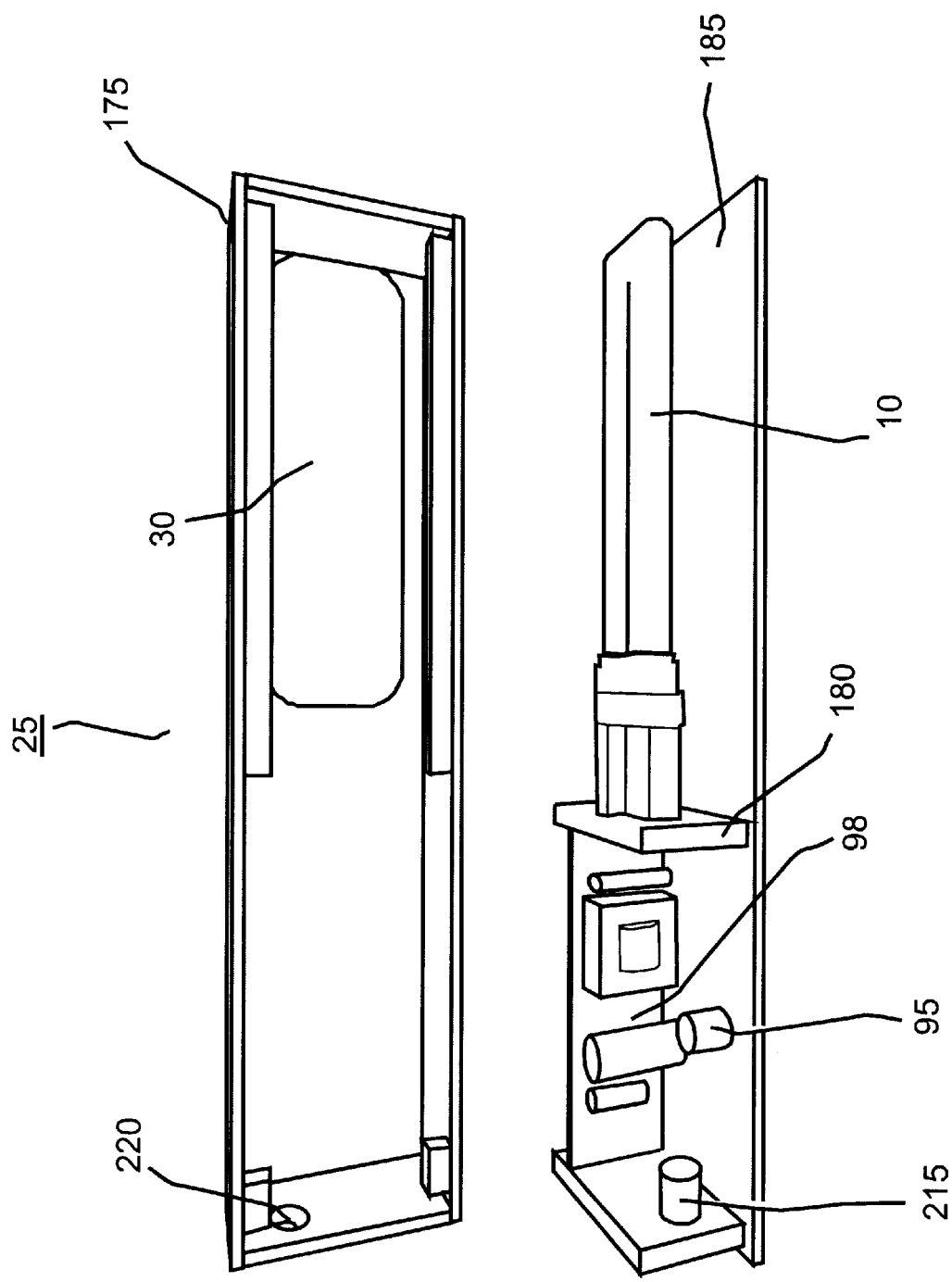
FIG. 12 is a perspective view of a handheld unit of this invention.

FIG. 12 is a perspective view of a handheld unit 25 of this invention designed for compactness so that the unit can be easily handheld. Preferably, the unit uses replaceable components and in a preferred embodiment has dimensions of approximately (L ×W ×H): 27.94 cm×6.35 cm×3.81 cm (11 in. ×2.5 in. ×1.5 in.). The unit comprises upper casing 175, containing first filter 30 and diffuser (not separately shown), on/off switch 95, DC ballast 98 and DC input socket 215. The light source 10 is removably mounted in lamp ballast mounting panel 180 in lower casing 185 designed to fit and be held by screws or latching means (not shown) into upper casing 175 so that first filter 30 is positioned directly over light source 10 when the unit is assembled. The unit also includes a DC input jack holder 220 to allow connection to a plug-in wall transformer to transform AC to DC.

The devices of this invention may be powered by AC or DC power using either a magnetic, electronic or DC ballast to drive the light sources. A 12-Volt DC power supply is preferred, as 12 V is significantly safer than 120 V. By connecting the unit to an AC power source through a plug-in wall transformer or the like capable of converting AC to DC, the unit can be made adaptable to differing types of AC power available anywhere in the world. Consequently, each assembled unit is internally identical. In addition, the unit may be powered by rechargeable batteries. Such a feature is particularly useful for a hand lamp, e.g., for use in hospitals and investigations of environmental features, e.g., at crime scenes and on or from other planets.

For increased sensitivity, lamps backed by reflective silver metallic linings to reflect light may be used. Lamps using different phosphors and shapes, and different wavelengths to optimize viewing of fluorescence may also be used, for example custom-manufactured lamps. The first optical filter may comprise separate regions for different viewing activities, e.g., viewing dyes with different fluorescent properties, and the second filter may comprise corresponding separate regions for viewing fluorescent species and colored stains as ordinarily viewed with a standard light box. The first filter may comprise slots or other means for assuring placement with respect to a light box or may comprise other holders for the light source. The first filter may also be rotatable in order to economize on the footprint of the unit. The second filter may be attached to the light box by a hinged top panel with slots for different filters if desired.

SYBR Green and SYBR Gold of Molecular Probes, Inc., of Eugene OR are preferred stains for DNA. They are more sensitive for detection of DNA than ethidium bromide and less mutagenic. In addition, if SYBR Green is used as a pre-stain, the cost per gel is comparable to that of using ethidium bromide. This stain does not interfere with post-gel manipulations of stained DNA, and if necessary, can be removed by ethanol precipitation.

A preferred embodiment of the transilluminator of this invention comprises a 14×21 cm viewing surface convenient for viewing smaller size gels. Larger viewing surfaces, such as 28×42 cm may be used for multiple and extra large gels. It is economically feasible using this invention to make transilluminators that are far larger than known UV boxes, i.e., over four feet long.

An optimum configuration of the device can be defined as the configuration of lamp and filters that results, for any given fluorophor, in the maximum amount of fluorescence and the minimum amount of lamp light reaching the human viewer or detector.

The process of optimization begins with a consideration of the optical properties of the particular fluorophor to be detected:

(a) The lamp should produce its maximum light intensity at wavelengths within the excitation spectrum of the fluorophor.

(b) The first filter should transmit the maximum amount of light at wavelengths within the excitation spectrum of the fluorophor. Filters of the preferred embodiments hereof transmit over 70% light in this region.

(c) The second filter should transmit the maximum amount of light at wavelengths within the emission spectrum of the fluorophor. In practice, filters of the preferred embodiments hereof transmit over 95% of the light in this region.

At the same time that excitation light to, and emitted light from, the fluorophor are maximized, it is essential to keep the light from the lamp that reaches the viewer to a minimum. This involves the following considerations:

(a) A lamp that produces minimal light intensity outside the excitation region of the fluorophor.

(b) The first filter should absorb as much as possible of the lamp light with wavelengths outside the excitation spectrum of the fluorophor. Filters of the preferred embodiments hereof absorb about 99.99% of the light in this region.

(c) The second filter should absorb as much as possible of the lamp light with wavelengths outside of the emission spectrum of the fluorophor. Filters of the preferred embodiments hereof absorb about 99.9% of the light in this region.

(d) The absorbing wavelength regions of the two filters must cross over such that the sum of the absorbances of the two filters in the crossover region results in as much as possible of the lamp light in this region being absorbed. In practice, the best filter combinations found so far absorb about 99.9% of the light in this region.

(e) If the first filter transmits lamp light in a region outside the excitation or emission regions of the fluorophor, then the second filter must absorb this light.

(f) If the second filter possesses intrinsic fluorescence, it should also comprise an auxiliary second filter placed between it and the light source to filter out light which excites it to fluoresce.

In optimizing the system for the detection of a particular fluorophor, a lamp containing a specially designed phosphor may be used, or filters containing specially designed pigments may be used, as may be readily made and assembled by one skilled in the art without undue experimentation.

Using readily available components, the following optimal configuration has been established for a light box to detect DNA fragments separated by gel electrophoresis and subsequently stained with SYBR Green I or ethidium bromide:

(a) lamp: Panasonic FPL28EB (available from Matsushita Home and Commercial Products Company, Secaucus, N.J.) or Sylvania CF 9 DS/blue (b) first filter: Acrylite #668-0GP (c) second filter: Perspex® #300

With these components it is possible to construct a transilluminator that provides a comparable level of sensitivity for the detection of stained DNA to that of a conventional UV transilluminator, as described in the Example below (see Table 7).

This configuration of lamp and filters is also appropriate for detecting other fluorophors with similar excitation and emission properties to SYBR Green I and ethidium bromide, such as SYPRO Orange, Vistra Green, Vistra ECF substrate, GelStar, fluorescein and derivatives, and eosin and derivatives, and rhodamine and derivatives.

The principles described herein can be used to make a large number of different devices using various arrangements of the components.

For example, FIG. 13 shows a scheme for a transilluminator for viewing fluorescent materials in gels and other transparent media. In this embodiment, light sources 10 and first optical filter 30 are contained in a holder or light box 15, atop which the fluorophor-containing material 50 is placed. Second optical filter 60 is placed over the fluorophor-containing material 50. Light in the exciting wavelength range hits first filter 30 to filter out other wavelengths, and passes into medium 50 causing fluorophors therein to fluoresce, emitting light in the emitted wavelength range which, mixed with light in the exciting wavelength range, passes through second optical filter 60 where light in the exciting wavelength range is filtered out, leaving substantially only light in the emitted wavelength range to strike the light detector 90.

FIG. 14 shows a scheme for an epi-illuminator for top illumination for viewing fluorescent materials in opaque media such as thin-layer chromatography plates. In this instance, light from the light sources 10 held in light box 15 passes through first optical filter 30, to excite fluorophors in medium 50 to emit light in the emitted wavelength range which passes through second filter 60 placed at an angle (preferably, but not necessarily 90°) to first filter 30 for filtering out wavelengths other than those in the emitted wavelength range, after which the light in the emitted wavelength range strikes the light detector 90.

FIG. 15 shows a scheme for viewing the position of fluorescent materials during column chromatography. In this case, a light box 15 containing light sources 10 and first filter 30 is placed next to the fluorophor-containing material 50, a column chromatograph. Second filter 60 is placed on the opposite side of the column. Light passes through the first filter 30, hits the column 50, and passes through second filter 60 to the light detector 90.

FIG. 16 shows a gel electrophoresis apparatus in which the two plates containing the gel also act as the two filters, allowing fluorescent materials to be viewed continuously during electrophoresis. Light box 15 containing light sources 10 holds first filter 30 in place. First filter 30 and second filter 60 act as the two plates holding the gel, i.e. the fluorophor-containing material 50. The light detector 90 is placed so as to receive light passing from the light sources 10 through first filter 30, the fluorophor-containing material 50 and second filter 60. Preferably, the horizontal electrophoresis transilluminator of this invention has a footprint of about 25×10 cm, and is the same size as an ordinary gel box. Since the viewer can continuously monitor the progress of a DNA fractionation, a gel only needs to be run until the DNA band(s) of interest are separated, thus in many cases, gel running times can be cut to fifteen to twenty minutes. In addition, DNA bands can be excised out of the gel in the electrophoresis unit, avoiding the danger of damaging the gel during transfer to a separate transilluminator.

FIG. 17 shows a thin-layer chromatography apparatus in which the filters are an integral part of the apparatus, allowing fluorescent materials to be viewed during thin-layer chromatography. In this case, first filter 30 is an integral part of light box 15 containing light source 10, which is detachably connected to a container into which the fluorophor-containing material 50 is placed. One side of the container comprises second filter 60. As in FIG. 11, light from light source 10 passes through first filter 30 to strike the fluorophor-containing material 50, and the fluorescence passes through second filter 60 and reaches the light detector 90.

FIG. 18 shows a handheld unit in combination with glasses 28 containing the second filter 60 worn by a human viewer. The eye of the viewer, or a mechanical light detector 90, is covered by a lens or lenses, shown as part of glasses 28 containing second filter 60. Light from light source 10 in handheld unit 25 passes through first filter 30 also comprised in handheld unit 25, then passes through the fluorophor-containing material 50 and second filter 60 comprised in glasses 28 to reach the viewer's eye or light detector 90. This embodiment is useful for a transparent medium. In alternative embodiments involving an opaque medium, the handheld unit 25 may be placed with respect to the fluorophor-containing material 50 so that light from light source 10 hits medium 50 and fluorescence emitted passes through to second filter 60 and light detector 90. The light source 10 may operate on DC or AC current. As a DC unit, handheld unit 25 may be powered by rechargeable batteries and thus run in remote locations if desired.

The handheld unit provides versatility for viewing fluorophors in both "open" systems such as agarose gels, nitrocellulose and polyvinyl difluoride (PVDF) membranes and thin layer chromatography (TLC) plates, as well as "closed" systems such as plastic and glass tubes, 96-well plates, chromatography columns, and sodium dodecyl sulfate polyacrylamide gel electrophoresis (SDS PAGE) gels and any kind of gel during electrophoresis. Using visible light, fluorophors can be viewed through a wide range of transparent or semi-transparent materials such as glass, polystyrene, polyethylene, polypropylene or acrylic. For example, in 1.5 mL polypropylene centrifuge tubes, using a handheld embodiment as described herein, fluorescein can be detected with eight times more sensitivity than using a UV lamp such that concentrations as low as 25 nmol/L may be detected, whereas using UV light at 360 and 312 nm, about 200 nmol/L is the lowest detectable concentration of fluorescein, and using UV light at 254 nm, over 1000 nmol/L of fluorescein must be present to be detected.

In "open" systems such as agarose gels, nitrocellulose membranes and TLC plates, fluorescein has been found to be detectable at very low concentrations. For example, on PVDF membranes, the visual detection limit is around 12 femtomoles of fluorescein, about twice the sensitivity achieved using UV light.

FIG. 19 shows a transilluminator of this invention comprising a light box 15 containing light sources 10 and first filter 30 atop which is placed the fluorophor-containing material 50. Handheld wand 210 comprising second filter 60 may be manually passed over the fluorophor-containing material 50 and sends image data 170 to a detector (not shown). The viewer 90, shown as a human eye wearing glasses also containing second filters 60, is able to directly view the fluorescence to aid in directing the wand over the fluorophor-containing material.

Figure 20:
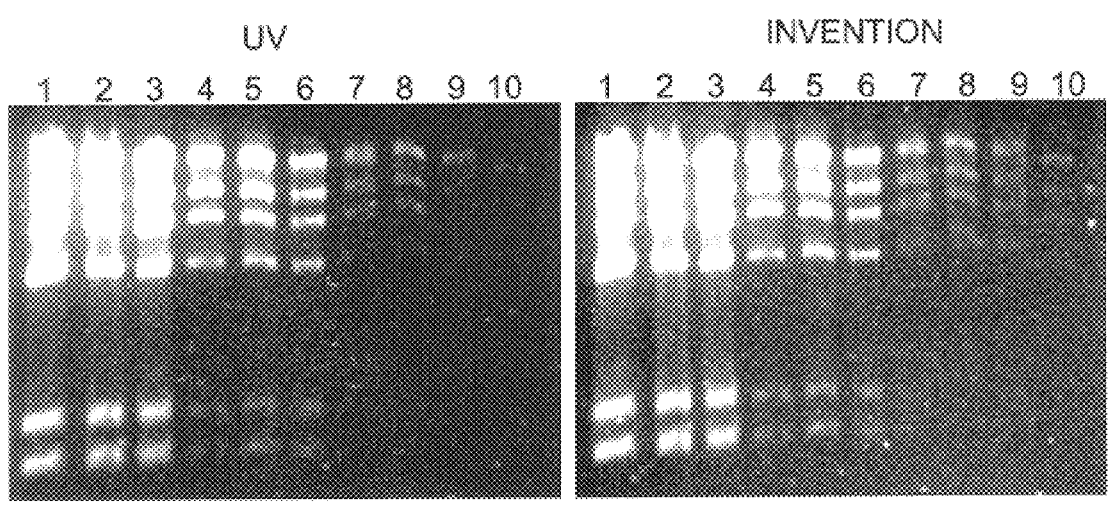
FIG. 20 compares SYBR Gold-stained DNA gels on a 312 nm UV transilluminator and on a transilluminator of this invention.

FIG. 20 shows a gel comparing SYBR Gold-stained DNA on a 312 nm UV transilluminator (left panel) and a transilluminator of this invention. Various amounts of λ DNA cut with HindIII were separated by gel electrophoresis and the gel stained with SYBR Gold. The gels were then photographed on a 312 nm UV transilluminator (left) or a transilluminator of this invention (right). As can be seen, the transilluminator of this invention provides greater sensitivity.

Figure 21:
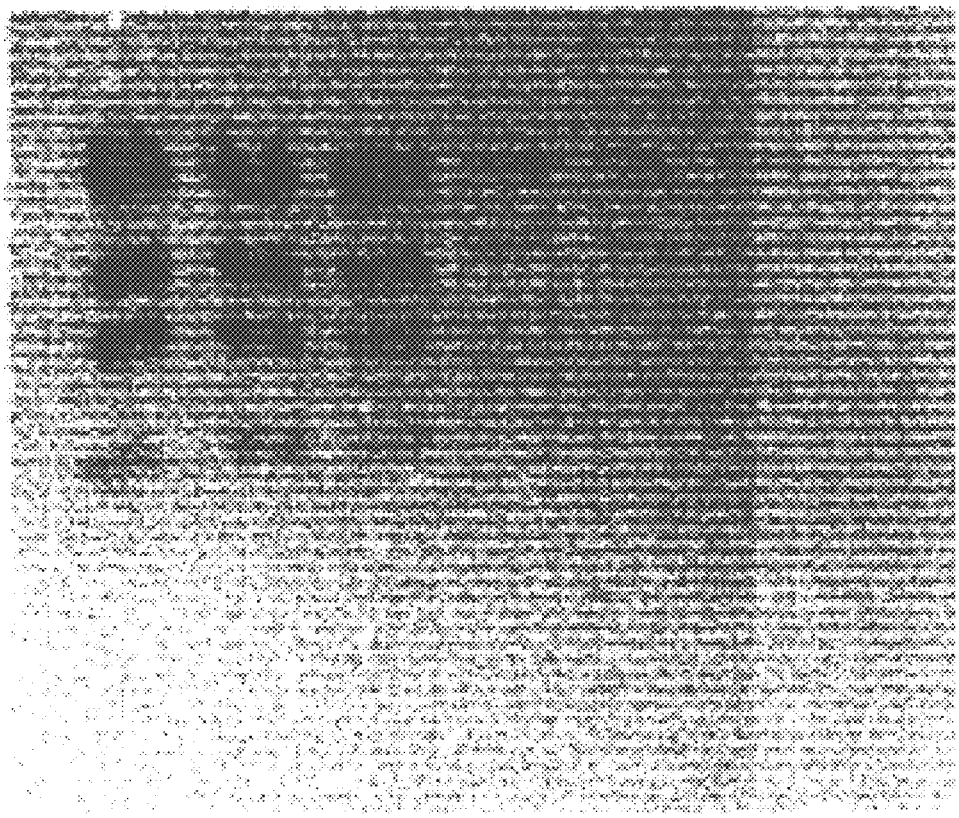
FIG. 21 shows a SYBR Gold-stained DNA gel image captured by computer scanning.

FIG. 21 shows the SYBR Gold gel of image shown in FIG. 20 (right side) made using a transilluminator of this invention and captured using a computer scanner. The original colored image was converted to grayscale and reversed.

Figure 22:
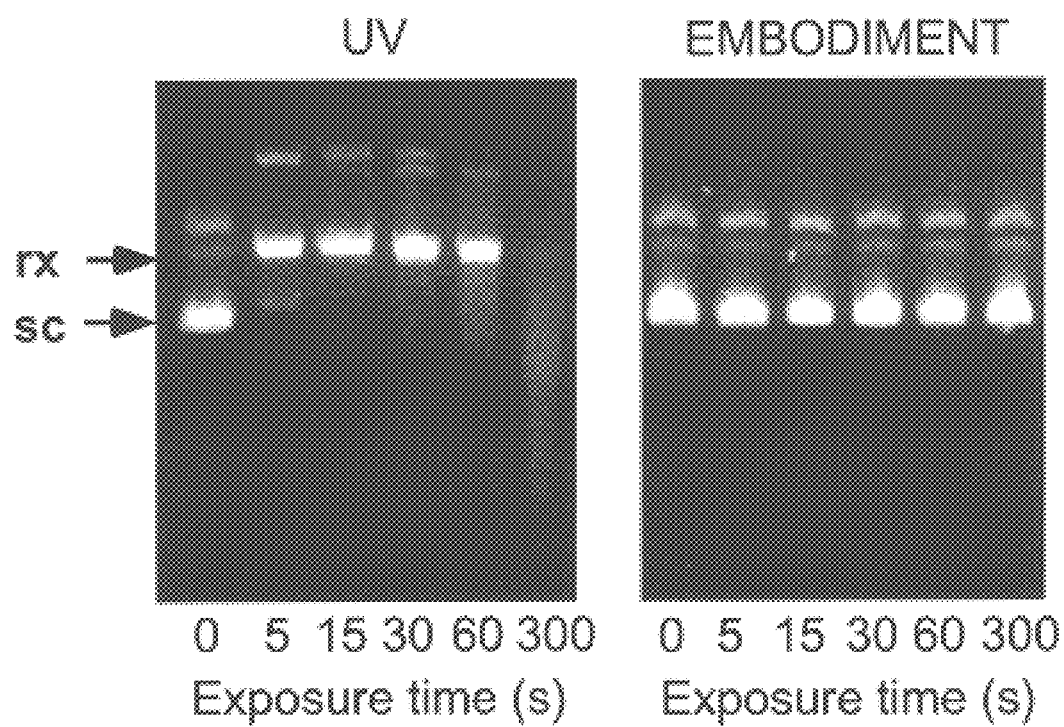
FIG. 22 shows gels comparing DNA degradation using a 312 nm UV transilluminator with DNA degradation using a transilluminator of this invention.

FIG. 22 shows gels comparing DNA degradation using a 312 nm UV transilluminator (right side) with that using a transilluminator of this invention. 100 ng of supercoiled (sc) plasmid pBR322 containing SYBR Green I was placed on either an embodiment (F40T12/BBY +#668 filter) or a 312 nm UV transilluminator (UV) for various times. The DNA was then digested with T4 endonuclease V which excises T:T dimers. The DNA was then run on a 0.7% agarose gel and photographed. It is clear that as little as a 5 second exposure to UV light is sufficient to convert almost 100% of the plasmid into the relaxed (rx) form, and after 300 seconds, the DNA is completely fragmented. In contrast, a 300 second exposure on the embodiment of this invention resulted in no detectable alteration to the plasmid.

Figure 23:
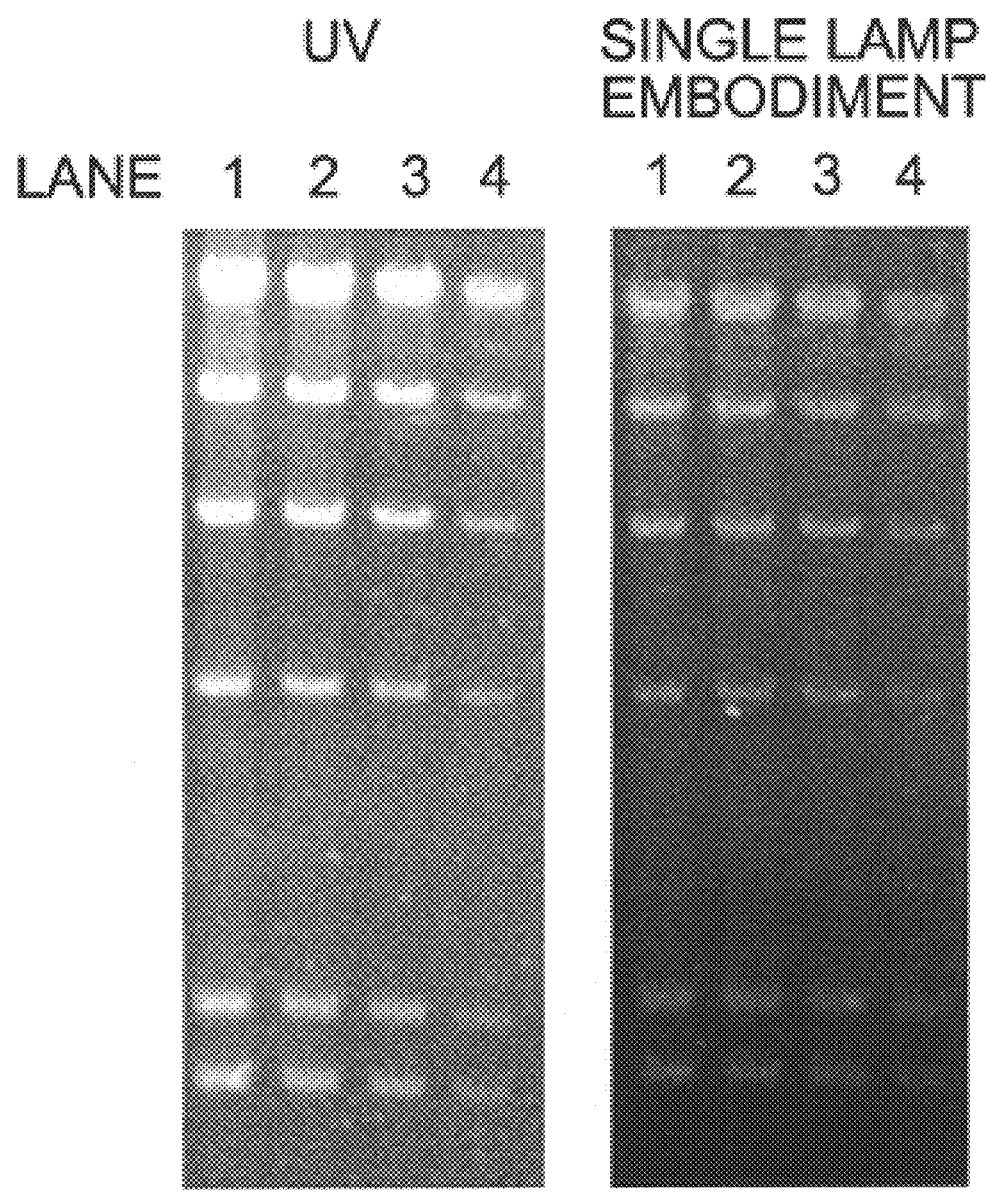
FIG. 23 compares ethidium bromide-stained DNA gels on an ultraviolet transilluminator (left side) and on a transilluminator of this invention (right side).

FIG. 23 shows gels comparing DNA stained with ethidium bromide using a standard UV transilluminator (left side) and a transilluminator of this invention (right side). As will be appreciated by those of skill in the art, the second filter shown in any of the above-described embodiments may be provided in the form of lenses for glasses or as attachments to mechanical light detectors rather than as a filter sheet or plate as shown. Further the devices can be configured with interchangeable filters or side-by-side filters to allow different fluorophors to be detected with maximum sensitivity. Lamps may be constructed to provide wavelengths optimized for each system, all as may be readily understood by those of skill in the art following the teachings provided herein.

EXAMPLES

Example 1

Sensitivity

The sensitivity of an optimized device of this invention was measured by detection of known quantities of DNA on gels stained with SYBR Green I and ethidium bromide, both by eye and by photography. What is seen by the eye and what is recorded on photographic film are not necessarily one and the same, especially when using black-and-white photography. For example, photographic film is able to accumulate an image over many seconds and, after processing, the image can be quantitated. On the other hand, the interpretative skill of the human eye when directly viewing an image is unparalleled. Though scientists use photographs of DNA gels for their laboratory records and for detailed analysis such as calculation of the sizes of DNA fragments, much of the analysis of a DNA band pattern on a gel is achieved using the naked eye. Furthermore, the excision of gel slices containing DNA is always done by eye. Therefore, it is important that the sensitivity of any apparatus for visualization of DNA in gels be documented and optimized for human eye and photographic detection methods separately.

The light-box used was an Apollo 100 obtained from OfficeMax, Denver, Colo. It came equipped with an F15T8DRWG fluorescent tube. This box was convenient for testing 45.72 cm (18 in.) fluorescent tubes such as the Osram F15T8D and Osram F15T8BLK. Other lamps were accommodated in makeshift housings.

Fluorescent tubes were obtained from Environmental Lighting, Denver, Colo. (Osram F15T8D, Osram F15T8BLK, Phillips F40B and Sylvania CF9DS/blue lamps) and U.S. Aquarium, Denver, Colo. (Panasonic FPL28EB lamps).

The gelatin filters used were obtained from Mike's Camera, Boulder, Colo., or from Wasatch Photographic, Denver, Colo., and included Kodak Wratten gelatin filters #12 (yellow), #21 (amber), #98 (blue) and #47 (blue) and Lee gelatin filters #15 (amber) and #21 (amber).

The acrylic filters used were obtained from either SS Plastics, Englewood, Colo., Fantastic Plastic, Englewood, Colo., or Colorado Plastic, Boulder, Colo., and included Acrylite #408-5GP (amber), Acrylite #668-0GP (blue), RAM #UM 2119 (amber), Dupont Lucite L #AM2422 (amber) and Dupont Lucite L #AM2424 (blue). In addition, amber filter Perspex® #300 was obtained from Amari Plastics, Bristol, UK. All American acrylic filters were used in 0.318 cm (0.125 in.) thick sheets except the 668-0GP blue which was used in both 0.318 cm (0.125 in.) and 0.635 cm (0.25 in.) thicknesses. The British materials were 3 and 6 mm.

The fluorescent dyes ethidium bromide, SYBR Green I and SYBR Gold were obtained from Molecular Probes Inc., Eugene, Oreg. All other chemicals were obtained from Boehringer Mannheim Corporation, Indianapolis, Ind. or Sigma Corporation, St. Louis, Mo.

Three samples of λ DNA (1 μg 0.1 μg and 0.01 μg) cut with the restriction enzyme EcoRI were electrophoresed in duplicate on a 0.7% agarose gel in 40 mmol/L tris acetate buffer (TAE), pH 7.8; 1 mmol/L ethylene diamine tetraacetic acid (EDTA) at 85 V for 90 minutes. The gel was then cut in half. One half of the gel was stained in a 1:10,000 dilution of SYBR Green I in TAE for 30 minutes at room temperature, and the other half was stained in 0.5 μg/mL solution of ethidium bromide in TAE under the same conditions. The gels were stored at 4° C.

For reference purposes, the gels were photographed on a UVP model #C-63 UV transilluminator (302 nm illumination) (Ultraviolet Products, Inc., Upland, Calif.) using Polaroid 667 film. The exposure time was 0.5 seconds and the f-stop was 5.5. A Kodak Wratten #12 filter was placed on top of the gel. The camera was an oscilloscope camera C27 (Tektronix Inc., Portland, Oreg.).

In order to determine the optimal configuration of filters and lamps, a prototype visible light transilluminator was constructed according to the scheme illustrated in FIG. 1 and described above. The gelatin filters were enclosed in clear, transparent acrylic sheets to protect them. All filters were enclosed in cardboard frames to prevent light leakage around the edges. A black-out cloth was also used to eliminate stray light from the lamp.

A variety of lamps and filters were placed in the apparatus and the DNA bands in the gels were visualized and photographed in a dimly lit room. No additional filter was used with the camera.

In order to compare the new transilluminator with the conventional UV model, from the known sizes of the fragments generated by EcoRI digestion of the λ DNA, the amount of DNA in each band on the agarose gel was calculated. The amounts ranged from 410 ng to 0.7 ng per band. A complete listing is given in Table 3.

To provide a standard measure of detectability, the stained gel was first placed on a standard 302 nm UV transilluminator. The DNA bands were visible using the naked eye down to the 0.9 ng level when stained with SYBR Green I, and 1.4 ng when stained with ethidium bromide (Table 4). In a photograph, the sensitivity was marginally lower: 1.5 ng for SYBR Green I and 4.1 ng for ethidium bromide. The slightly greater visibility of the SYBR Green-stained DNA is probably due to a lower background light level from the gel itself. The ability to detect as little as 0.9 ng of DNA serves as a reference point for the sensitivity of the constructed visible light transilluminator.

The gels were then placed on the new transilluminator and various combinations of blue filters underneath the gel and amber filters above the gel were tried together with different lamps. Both naked-eye and photographic film results are given in Tables 5 and 6.

Of the blue filters, #2424 transmits excessive amounts of red light and its use was not pursued any further. The #98 transmits blue light of significantly shorter wavelengths than either #668-0GP or #47, both of which appear to have very similar transmission characteristics. The shorter wavelength transmission characteristics of #98 mean that it can be used with the yellow emission filers (e.g., #12), whereas #668-0GP and #47 are optimal with the orange emission filters.

With either #668-0GP or #47 as excitation filter, it was found in general that the use of a single orange filter on the emission side was insufficient, either because too much background light was transmitted to allow detection of the fluorescent DNA, or because the filter possessed intrinsic fluorescence which obscured the DNA fluorescence. This latter problem was particularly noticeable with filters #408 and #2422.

The filter fluorescence could be overcome by using two emission filters in-line. Thus, by placing a #2119 or Lee #21 before a #408 or #2422 relative to the lamp, it was possible to significantly reduce the fluorescence of the second emission filter.

Filter Perspex® #300 did not possess any intrinsic fluorescence and, in combination with #668-0GP as the excitation filter, yielded the best overall results.

The photography involved significantly different exposure times: typically, 0.5 seconds for UV, 5 seconds for the F40B, and 15 seconds for the F15T8D. Using the F15T8D, the detectability of SYBR Green-stained DNA in photographs was approximately the same using either a five second or a 15 second exposure time. However, using a five second exposure, the ethidium bromide-stained DNA was essentially undetectable in photographs.

A useful arrangement involves excitation filter #668-0GP and emission filter #300 (Table 7). Either lamp F15T8D or F40B yields similar levels of DNA detectability to the naked eye. For photographic purposes, the F15T8D requires a 15 second exposure to adequately reveal EB-stained DNA whereas the F40B requires five seconds. This difference is unlikely to be of any practical significance. A lamp readily available in a size that fits the light-box is preferred.

The smallest amount of DNA visible to the naked eye using an F15T8D lamp and #668-0GP and #300 filters is 0.7 ng if stained with SYBR Green I. This is comparable to the detection level of the UV transilluminator (0.9 ng). With ethidium-stained DNA the white light (WL) transilluminator is somewhat less sensitive with a 4.1 ng detection level, compared to the UV transilluminator's ability to detect 1.4 ng.

By photography, the situation is reversed: the detection level of 0.7 ng for SYBR Green-stained DNA using the WL transilluminator is somewhat better than the UV transilluminator (1.5 ng). With ethidium bromide-stained DNA, both transilluminators are of comparable sensitivity and can detect 4.1 ng of DNA.

TABLE 3

Amounts of DNA present in the gel after electrophoresis.

| Band No. | Size (base pair) | ng of DNA per band | | |
|---|---|---|---|---|
| | | 1 μg load | 0.1 μg load | 0.01 μg load |
| 1 | 21220 | 410 | 41 | 4.1 |
| 2 | 7420 | 140 | 14 | 1.4 |
| 3 + 4[1] | 5800 + 5640 | 220 | 22 | 2.2 |
| 5 | 4880 | 90 | 9 | 0.9 |
| 6 | 3530 | 70 | 7 | 0.7 |

[1]Bands #3 and #4 were not resolved on the gel.

TABLE 4

Detectable levels of DNA using a UV transilluminator

| Method of Detection | Amount of DNA detectable (ng) | |
|---|---|---|
| | SYBR Green I | Ethidium bromide |
| Eye | 0.9 | 1.4 |
| Photo[1] | 1.5 | 4.1 |

[1]The exposure time for the photographs was 0.5 second.

TABLE 5

Direct Visual Detection of Fluorescent DNA[1]

| | Blue Filter | | | | | | | | | | | |
|---|---|---|---|---|---|---|---|---|---|---|---|---|
| | 47 | | | | 98 | | | | 668-0GP | | | |
| | WL | | BL | | WL | | BL | | WL | | BL | |
| Amber Filter | SG | EB | SG | EB | SG | EB | SG | EB | SG | EB | SG | EB |
| 12 + 15 | | | | | | | 0.9 | 41 | | | | |
| 2119 + 408 | 0.9 | 9 | 0.9 | 9 | | | 0.9 | 22 | 0.9 | 9 | 0.7 | 4.1 |
| 2119 + 2422 | 0.9 | 9 | 0.7 | 4.1 | | | 0.9 | 22 | 0.9 | 9 | 0.7 | 4.1 |
| 21 + 408 | 0.9 | 22 | 0.7 | 9 | | | | | 0.7 | 9 | 0.7 | 4.1 |
| 300 | 0.7 | 9 | 0.7 | 9 | | | 0.9 | 22 | 0.7 | 4.1 | 0.7 | 4.1 |

[1]This table documents the minimum amount of DNA (in nanograms) visible on the gel using various filter combinations. WL, white fluorescent lamp F15T8D; BL, blue fluorescent lamp F40B; SG, SYBR Green I; EB, ethidium bromide. Blank entries were not measured.

TABLE 6

Photographic Detection of Fluorescent DNA[1]

| | Blue Filter | | | | | | | | | | | |
|---|---|---|---|---|---|---|---|---|---|---|---|---|
| | 47 | | | | 98 | | | | 668-0GP | | | |
| Amber | WL | | BL | | WL | | BL | | WL | | BL | |
| Filter | SG | EB | SG | EB | SG | EB | SG | EB | SG | EB | SG | EB |
| 12 + 15 | | | | | | | | | | | | |
| 2119 + 408 | | | | | | | | | 0.7 | 9 | | |
| 2119 + 2422 | | | | | | | | | 0.9 | 9 | 0.9 | 4.1 |
| 21 + 408 | | | 1.0 | 9 | | | | | 0.7 | 9 | 0.9 | 9 |
| 300 | 1.0 | 9 | 1.0 | 9 | | | | | 0.7 | 4.1 | 0.7 | 4.1 |

[1]This table documents the minimum amount of DNA (in nanograms) detectable in photographs of the gel. WL, white fluorescent lamp F15T8D; BL, blue fluorescent lamp F40B; SG, SYBR Green I; EB, ethidium bromide. The exposure times for the WL and BL photographs were 15 seconds and five seconds, respectively.

TABLE 7

Detectable Levels of DNA Using the Transilluminator[1]

| Method of Detection | Amount of DNA detectable (ng) | |
|---|---|---|
| | SYBR Green I stained gel | Ethidium Bromide stained gel |
| Eye | 0.7 (0.9) | 4.1 (1.4) |
| Photo | 0.7 (1.5) | 4.1 (4.1) |

[1]The transilluminator was equipped with an F15T8D lamp and #668-0GP (blue) and #300 (amber) filters. For the photographic detection the exposure time was 15 seconds. The amounts of DNA detectable using a UV transilluminator are in parentheses. (See Table 3.)

Example 2

Blue Compact Fluorescent Lamps and SYBR Gold

Various dilutions of λ DNA cut with HindIII (Boehringer Mannheim) in 10 mmol/L Tris-Cl, 1 mmol/L EDTA were incubated at 60° C. for three minutes. The samples were placed on ice and sample loading buffer (0.25% bromophenol blue, 0.25% xylene cyanol, 15% Ficoll type 400 in 10 mmol/L Tris-Cl, 1 mM EDTA, pH 7.5) was added to each mix. Various amounts of the DNA samples (from 428 ng to 0.85 ng) were loaded onto a 1% agarose gel 7.62 cm (3 in.)×12.70 cm (5 in.) in 89 nmol/L Tris borate, pH 7.82, and 2 mmol/L EDTA (TBE). The gel was run at 80 V for two hours and then placed in 100 mL of 1:10000 dilution (in TAE) of SYBR Gold for 30 minutes. The gel was photographed using a Polaroid® camera (Polaroid Corporation, Cambridge, Mass.) with Polaroid 667 film on either a Fisher UV 312 nm variable intensity transilluminator (Fischer Scientific, Pittsburgh, Pa., Model No. FBTTV-816), set to maximum intensity in all cases, a Wratten #12 on the camera, f-stop =5.6, exposure time =⅛ second) or an embodiment of the present invention equipped with a CF9DS/blue lamp, a #668-0GP first filter, and a #300 second filter (no additional filter over the camera, f-stop =5.6, exposure time=1 second).

The photographs are shown in FIG. 20. Table 8 shows the amount of DNA in each band.

TABLE 8

The Amount of λ DNA cut with HindIII on the Gel. The amounts of DNA listed are in ng.

| Lane # | 1 | 2 | 3 | 4 | 5 | 6 | 7 | 8 | 9 | 10 |
|---|---|---|---|---|---|---|---|---|---|---|
| DNA Load | 428 | 214 | 107 | 54 | 27 | 13 | 6.7 | 3.3 | 1.7 | 0.85 |
| Band 1 | 204 | 102 | 51 | 26 | 13 | 6.4 | 3.2 | 1.6 | 0.80 | 0.40 |
| Band 2 | 83 | 42 | 21 | 10 | 5.2 | 2.6 | 1.3 | 0.65 | 0.32 | 0.16 |

TABLE 8-continued

The Amount of λ DNA cut with HindIII on the Gel. The amounts of DNA listed are in ng.

| Lane # | 1 | 2 | 3 | 4 | 5 | 6 | 7 | 8 | 9 | 10 |
|---|---|---|---|---|---|---|---|---|---|---|
| Band 3 | 58 | 29 | 14 | 7.2 | 3.6 | 1.8 | 0.90 | 0.45 | 0.22 | 0.11 |
| Band 4 | 38 | 19 | 10 | 4.8 | 2.4 | 1.2 | 0.60 | 0.30 | 0.15 | 0.075 |
| Band 5 | 20 | 10 | 5.1 | 2.6 | 1.3 | 0.64 | 0.32 | 0.16 | 0.080 | 0.040 |
| Band 6 | 18 | 8.9 | 4.5 | 2.2 | 1.1 | 0.56 | 0.27 | 0.13 | 0.070 | 0.035 |

In the photograph taken using the embodiment of this invention, it is possible to visualize band 3 in lane 10. This corresponds to 110 pg of DNA. In the photograph taken using the UV transilluminator it is possible to see band 2 in lane 10. This corresponds to 160 pg of DNA.

By eye, lane 10, band 4 (75 pg) was just at the limit of visibility for both devices.

Example 3

Ethidium Bromide Gel

λ DNA cut with HindIII (Boehringer Mannheim) in 10 mmol/L Tris-Cl, 1 mmol/L EDTA was mixed with sample loading buffer and various amounts of DNA (from 125 ng to 15.6 ng) were loaded onto a 0.7% agarose gel (7.62 cm [3 in.]×12.70 cm[5 in.]) in TAE. Ethidium bromide was added to both the gel and running buffer to a final concentration of 0.25 μg/mL. The gel was run at 110 V for two hours and then examined by eye and photographed using a Polaroid camera with Polaroid 667 film on either a UV 312 nm transilluminator (Fisher Scientific) set to maximum lamp intensity using a red Tiffen 40.5 mm 23A filter (Tiffen Manufacturing Corp., Hauppauge, N.Y.) on the camera (f-stop =5.6, exposure time =2 seconds) or an embodiment of the present invention as depicted in FIG. 9 equipped with a CF9DS/blue lamp, a #668-0GP first filter, and a Perspex® #300 second filter. A Wratten #21 (Kodak) was used as an additional second filter for photography (f-stop =5.6, exposure time =30 seconds). The gel was also observed and photographed (f-stop =5.6, exposure time =10 seconds) on an embodiment identical to the above except that it contained two CF9DS/blue lamps.

The photographs of the gel are shown in FIG. 23. Table 9 shows the amount of DNA in each band.

TABLE 9

The amount of λ DNA cut with Hind III on the Gel. The amounts of DNA listed are in ng.

| Lane # | 1 | 2 | 3 | 4 |
|---|---|---|---|---|
| DNA load | 125 | 63 | 31 | 16 |
| Band 1 | 60 | 30 | 15 | 7.5 |
| Band 2 | 24 | 12 | 6.1 | 3.0 |
| Band 3 | 17 | 8.5 | 4.2 | 2.1 |
| Band 4 | 11 | 5.6 | 2.8 | 1.4 |
| Band 5 | 6.0 | 3.0 | 1.5 | 0.75 |
| Band 6 | 5.2 | 2.6 | 1.3 | 0.65 |

By eye, using the UV transilluminator, it was possible to see 0.65 ng of DNA. Using the single lamp embodiment it was possible to see 2.4 ng of DNA, and using the twin lamp embodiment it was possible to see 1.2 ng of DNA. Overall, the viewability of the DNA bands in the twin lamp embodiment was better than in the single lamp version in that the eye did not take as long to adjust as it did to the lower light levels emanating from the single lamp version.

In the Polaroid photograph taken using the 312 nm UV transilluminator it is possible to see band 6 in lane 4. This corresponds to 0.65 ng of DNA. In the photograph taken using the single lamp embodiment it is possible to see the same band if the Polaroid film is exposed for 30 seconds. The twin lamp embodiment gave very similar DNA detectability results in the photograph but the exposure time required was only one third as long.

Example 4

Gel Scanning

The SYBR Gold-stained gel used in Example 2 was placed on an Astra 600S scanner (Umax Technologies, Inc., Fremont, Calif.) linked to a Power CenterPro™ 180 computer (PowerComputing, Round Rock, Tex.) running VistaScan V2.3.7 software (Umax Data Systems, Inc.). The amber filter Perspex #300 was placed on top of the scanner bed, the gel placed on top of the Perspex and, on top of that, a #668-0GP first filter and a CF9DS/blue lamp. The gel was scanned in color at 600 dpi using "transmissive mode" with VistaScan settings of 97, 9, 34 and 53 for highlight, shadow, brightness and contrast respectively.

FIG. 21 shows the resultant image enhanced using image manipulation software as found in Canvas 5.0 (Deneba Systems, Inc., Miami, Fla.). It is possible to see band 1 in lane 6. This corresponds to 6.4 ng of DNA.

Example 5

DNA Integrity

Supercoiled plasmid pBR322 was placed on either a transilluminator of this invention or a 312 nm UV transilluminator for various periods of time. The DNA was then digested with T4 endonuclease V which excises T:T dimers and run on a 0.7% agarose gel to allow quantitation of the amount of relaxed plasmid formed.

1 μg of supercoiled pBR322 in 100 μL of 50 mmol/L Tris, pH 7.5, 5 mmol/L EDTA was incubated with 1 μL of a 100-fold dilution of SYBR Green I (diluted in 50 mM Tris, pH 7.5, 5 mmol/L EDTA) on ice. This mixture was placed directly onto the surface of either an embodiment composed of an F40T12/BBY lamp (Interelectric Inc., Warren, N.J.) and a Cyro #668-0GP filter, or a 312 nm UV transilluminator. A "zero-time" aliquot of 10 μL was removed from the surface before turning on the transilluminator and stored in the dark on ice. Further 10 μL samples were removed at 5, 15, 30, 60 and 300 seconds.

1 μL of a 20-fold dilution (using 50 mM Tris, pH 7.5,5 mmol/L EDTA) of T4 endonuclease V (Epicentre, Madison, Wis.) was added to each 10 μL time-point and allowed to react for two hours, 37° C. This enzyme excises T:T dimers.

The samples were then run on a 0.7% agarose gel in TAE and the band pattern photographed.

The results are shown in FIG. 22. UV light is shown to be extremely damaging to DNA; after a mere five second exposure the supercoiled DNA is almost completely converted to the relaxed form, and after five minutes almost all the DNA has been converted into a low molecular smear. Using the transilluminator of this invention, however, essentially no DNA damage was detectable over the entire duration of the exposure (five minutes).

The invention maintains the integrity of the DNA samples. This feature of the invention provides for enhanced efficiencies in procedures where the integrity and information content of the DNA samples is important such as gene cloning and sequencing.

Example 6

Polarization

To test the ability of a pair of polarization filters to select for fluorescent light and to remove lamp light, an agarose gel containing various amounts of λ DNA restricted with HindIII and stained with SYBR Gold stain (the same gel used in Example 2) was viewed using several filter combinations. The light source was a CF9DS/blue lamp. The polarizing filters were from Visual Pursuits, Inc., Vernon Hills, Ill.

TABLE 10

| First filter | Second filter | ng DNA |
| --- | --- | --- |
| none | none | 26 |
| P* | P (parallel) | 83 |
| P | P (orthogonal) | 5.2 |

*P indicates a polarization filter from Visual Pursuits.

For photography using Polaroid 667 film it was found to be necessary to include a Wratten #21 filter to reduce the lamp light to levels at which the fluorescent DNA bands could be captured.

The lamp light was not completely eliminated by the two orthogonal polarizing filters, making the sensitivity of this embodiment relatively poor. The absorption spectrum of two orthogonal polarizing filters together revealed that a significant amount of blue light was transmitted ($\%T_{460\ nm}$=0.23%). This indicates that these particular polarizing filters are not polarizing the light in this wavelength range efficiently enough to be of much practical use. Filters which, in combination, have a %T of around 0.02% or less are required. Polarization of fluorescence may be used to distinguish between large and small fluorophor molecules, immobilized or free fluorophor molecules, or oriented/non-oriented molecules.

It should be understood that the visible light fluorometric detection system as specifically described herein could be altered without deviating from its fundamental nature. For example, different light sources, sets and types of filters could be substituted for those exemplified and described herein, so long as the light reaching the light detector, i.e., the viewer's eye or detection device, contains sufficient information about the light emitted from the fluorophors whose fluorescence is being visualized to allow viewing of an image of the pattern of fluorescence and so long as sufficient interfering light has been filtered out such that visualization is possible. It is therefore to be understood that within the scope of the appended claims, the invention may be practiced in ways other than as specifically described herein.

I claim:

1. A visible light transilluminator system for viewing one or more patterns of fluorescence emitted by fluorophors, capable of being excited by light of an excitation type and capable of emitting light of an emitted type, wherein at least a portion of said emitted type is of a wavelength different from said excitation type, said system comprising:
    a) a non-laser colored light producing element that produces light, at least a portion of which is capable of exciting said fluorophors;
    b) a first colored optical filter positioned between said light producing element and said fluorophors, wherein said first optical filter is capable of transmitting light of said excitation type and of preventing transmission of light of said emitted type; and
    c) a second colored optical filter positioned in optical communication with said fluorophors, wherein said second optical filter is capable of transmitting light from said fluorophors of said emitted type and of preventing transmission of light of said excitation type; said system being constructed and arranged such that patterns of fluorescence emitted by said fluorophors are viewable.

2. The transilluminator of claim 1 comprising a light detector.

3. The transilluminator of claim 1 wherein said first optical filter is blue or green and said light producing element appears blue to the eye.

4. The transilluminator of claim 3 wherein said second optical filter is yellow.

5. The transilluminator of claim 3 wherein said second optical filter is amber.

6. The transilluminator of claim 3 wherein said second optical filter is red.

7. The transilluminator of claim 1 wherein said first optical filter is blue or green and said light producing element appears green to the eye.

8. The transilluminator of claim 7 wherein said second optical filter is yellow.

9. The transilluminator of claim 7 wherein said second optical filter is amber.

10. The transilluminator of claim 7 wherein said second optical filter is red.

11. The transilluminator of claim 1 wherein said light producing element appears red to the eye.

12. The transilluminator of claim 11 wherein said second optical filter is red.

13. The transilluminator of claim 1 wherein said light producing element produces light with a maximal output over a wavelength range of approximately 380 nm to approximately 440 nm and said first filter is violet-blue.

14. The transilluminator of claim 13 wherein said second optical filter is yellow.

15. The transilluminator of claim 13 wherein said second optical filter is red.

16. The transilluminator of claim 13 wherein said second optical filter is amber.

17. The transilluminator of claim 1 wherein said light producing element produces light with a maximal output over a wavelength range of approximately 440 nm to approximately 470 nm and said first optical filter is blue.

18. The transilluminator of claim 17 wherein said second optical filter is yellow.

19. The transilluminator of claim 17 wherein said second optical filter is red.

20. The transilluminator of claim 17 wherein said second optical filter is amber.

21. The transilluminator of claim 1 wherein said light producing element produces light with maximal output over a wavelength range of approximately 460 nm to approximately 510 nm and said first optical filter is blue or blue-green.

22. The transilluminator of claim 21 wherein said second optical filter is yellow.

23. The transilluminator of claim 21 wherein said second optical filter is red.

24. The transilluminator of claim 21 wherein said second optical filter is amber.

25. The transilluminator of claim 1 wherein said light producing element produces light with maximal output over a wavelength range of approximately 500 nm to approximately 550 nm and said first optical filter is green or blue-green.

26. The transilluminator of claim 25 wherein said second optical filter is yellow.

27. The transilluminator of claim 25 wherein said second optical filter is red.

28. The transilluminator of claim 25 wherein said second optical filter is amber.

29. The transilluminator of claim 1 wherein said light producing element produces light with a maximal output over a wavelength range of approximately 550 nm to approximately 650 nm.

30. The transilluminator of claim 29 wherein said second optical filter is red.

31. The transilluminator of claim 29 wherein said second optical filter is amber.

32. A visible light photoluminescent imaging system for viewing one or more patterns of fluorescence emitted by fluorophors or a material containing fluorophors, capable of being excited by light of an excitation type and capable of emitting light of an emitted type, wherein at least a portion of said emitted type is of a wavelength different from said excitation type, said system comprising:

a) a non-laser colored light source comprising a light producing element that produces light, at least a portion of which is capable of exciting said fluorophors, and a first colored optical filter positioned between said light producing element and said fluorophors that is capable of transmitting light of said excitation type and of preventing transmission of light of said emitted type, wherein the non-laser light source produces light substantially free of light in the ultraviolet region; and b) a second colored optical filter positioned in optical communication with said fluorophors, wherein said second optical filter is capable of transmitting light of said emitted type from said fluorophors and of preventing transmission of said excitation light;

said system being constructed and arranged such that patterns of fluorescence emitted by said fluorophors are viewable.

33. The photoluminescent imaging system of claim 32 comprising a light detector positioned along an optical illumination axis defined by a notional line connecting said light source and said fluorophors.

34. The photoluminescent imaging system of claim 32 comprising a light detector positioned along a point not on an optical illumination axis defined by a notional line connecting said light source and said fluorophors.

35. The photoluminescent imaging system of claim 32 comprising a light detector in optical communication with said second filter and positioned sufficiently far from said fluorophors to provide spacial resolution of individual emitting fluorophors within said material containing fluorophors.

36. The photoluminescent imaging system of claim 32 wherein said light producing element comprises one or more lamps.

37. The photoluminescent imaging system of claim 32 wherein said light source and said second optical filter are comprised within an integrated horizontal gel electrophoresis unit.

38. The photoluminescent imaging system of claim 32 wherein said light source and said second colored optical filter are comprised within an integrated vertical gel electrophoresis unit.

39. The photoluminescent imaging system of claim 32 wherein said light source and said second colored optical filter are comprised within an integrated thin layer chromatography unit.

40. The photoluminescent imaging system of claim 32 wherein said light source and said second colored optical filter are comprised within an integrated fish tank.

41. The visible light photoluminescent imaging system of claim 32 wherein the colored light source produces light comprising substantially of light capable of exciting said fluorophors.

42. The visible light photoluminescent imaging system of claim 32 wherein the light producing element contains phosphors.

43. A visible light photoluminescent imaging system for viewing one or more patterns of fluorescence emitted by fluorophors, capable of being excited by light of an excitation type and capable of emitting light of an emitted type, wherein at least a portion of said emitted type is of a wavelength different from said excitation type, said system comprising:

a) a non-laser light source comprising a light producing element that produces light, at least a portion of which is capable of exciting said fluorophors, and a first optical filter positioned between said light producing element and said fluorophors that is capable of transmitting light of said excitation type and of preventing transmission of light of said emitted type, wherein the non-laser light source produces light substantially free of light in the ultraviolet region; and b) a second optical filter positioned in optical communication with said fluorophors, wherein said second optical filter is capable of transmitting light of said emitted type from said fluorophors and of preventing transmission of said excitation light;

said system being constructed and arranged such that patterns of fluorescence emitted by said fluorophors are viewable.

44. The transilluminator of claim 43 comprising one or more additional optical filters positioned in optical communication with said second optical filter.

45. The photoluminescent imaging system of claim 43 wherein said light producing element has a total power per square area less than approximately 0.072 W $cm^{-2}$.

46. The photoluminescent imaging system of claim 43 wherein said light producing element has a luminous flux less than approximately 2670 lumens.

47. The photoluminescent imaging system of claim 43 wherein said first optical filter and said second optical filter have a transmission area ranging from approximately 9 $cm^2$ to approximately 1180 $cm^2$.

48. The photoluminescent imaging system of claim 43 wherein said second optical filter is a short wavelength cutoff filter in the visible region.

49. The photoluminescent imaging system of claim 43 wherein said first optical filter is a long wavelength cutoff filter in the visible region.

50. The photoluminescent imaging system of claim 43 wherein said first optical filter and said second optical filter are cutoff filters in the visible region.

51. The visible light photoluminescent imaging system of claim 43 wherein the non-laser light source produces less ultraviolet light than a UV transilluminator.

52. A visible light photoluminescent imaging system for viewing one or more patterns of fluorescence emitted by fluorophors capable of being excited by light of an excitation type and of producing light of an emitted type, wherein at least a portion of said emitted type is of a wavelength different from said excitation type, said system comprising:
 a) a non-laser light source comprising a light producing element that produces light, a portion of which is capable of exciting said fluorophors, and a first optical filter positioned between said light producing element and said fluorophors, wherein said first optical filter is capable of transmitting light of said excitation type and of preventing transmission of light of said emitted type;
 b) fluorophors having a Stokes shift of less than 100 nm; and
 c) a second optical filter positioned in optical communication with said fluorophors, wherein said second optical filter is capable of transmitting light of said emitted type from said fluorophors and of preventing transmission of light of said excitation type;
said system being constructed and arranged such that patterns of fluorescence emitted by said fluorophors are viewable.

53. A method of viewing one or more patterns of fluorescence emitted by fluorophors capable of being excited by light of an excitation type and of producing light of an emitted type, wherein at least a portion of said emitted type is of a wavelength different from said excitation type, said method comprising:
 a) passing visible light substantially free of light in the ultraviolet region from a non-laser colored light source on to said fluorophors or a material containing said fluorophors, whereby said fluorophors emit light of said emitted type, wherein said colored light source comprises a light producing element that produces light, at least a portion of which is said excitation type, and a first colored optical filter positioned between said light producing element and said fluorophors, wherein said first optical filter is capable of transmitting light of said excitation type and of preventing transmission of light of said emitted type;
 b) passing said emitted light through a second colored optical filter, which is capable of transmitting light of said emitted type from said fluorophors and of preventing transmission of light of said excitation type, whereby an image of said patterns of fluorescence is formed; and
 c) viewing said image with a human eye and/or other light detector.

54. The method of claim 53 wherein said fluorophors are comprised in fluorescently stained DNA.

55. The method of claim 53 wherein said material containing fluorophors comprises at least one fluorescently labeled protein.

56. The method of claim 53 wherein said material containing fluorophors comprises at least one fluorescent protein.

57. The method of claim 53 wherein said fluorophors are comprised in a gel.

58. The method of claim 53 wherein said fluorophors are comprised in a living organism.

59. The method of claim 53 wherein said fluorophors are viewed in an array of test tubes.

60. The method of claim 53 wherein said fluorophors are comprised in fluorescent fish in a fish tank.

61. A visible light photoluminescent imaging system for viewing one or more patterns of fluorescence emitted by fluorophors capable of being excited by light of an excitation type and of producing light of an emitted type, wherein at least a portion of said emitted type is of a wavelength and polarization different from said excitation type, said system comprising:
 a) a non-laser light producing element that produces light, at least a portion of which is light of said excitation type;
 b) a first optical polarization filter positioned between said light producing element and said fluorophors, wherein said first filter is capable of transmitting polarized light of said excitation type having a first polarization orientation and capable of preventing transmission of light from the light-producing element having a polarization orientation different than said first polarization orientation; and
 c) a second optical polarization filter positioned in optical communication with said fluorophors, wherein said second filter is capable of transmitting polarized light of said emitted type having a second polarization orientation and preventing transmission of light of said excitation type and wherein said second polarization orientation is different than that of said first orientation and is different from the polarization orientation of light from said light producing element scattered by said fluorophors;
said system being constructed and arranged such that patterns of fluorescence, emitted by said fluorophors, of wavelengths different than that of light of said excitation type, are viewable.

62. The photoluminescent imaging system of claim 61 comprising a light detector.

63. A visible light photoluminescent imaging system for viewing one or more patterns of fluorescence emitted by fluorophors capable of being excited by light of an excitation type and of producing light of an emitted type, wherein at least a portion of said emitted type is of a wavelength different from said excitation type, said system comprising:
 a) colored non-laser exciting light substantially free of light in the ultraviolet region, at least a portion of which is of a wavelength in the range of said excitation type;
 b) a first colored optical filter positioned in optical communication with said fluorophors or a material containing said fluorophors, through which light of said excitation type is transmitted, wherein said first optical filter is capable of transmitting light of said excitation type and of preventing transmission of light of said emitted type; and
 c) a second colored optical filter, positioned in optical communication with said fluorophors, wherein said second colored filter is capable of transmitting light of said emitted type from said fluorophors and of preventing transmission of light of said excitation type;
said system being constructed and arranged such that patterns of fluorescence emitted by said fluorophors are viewable.

64. The photoluminescent imaging system of claim 63 comprising a light detector.

65. A visible light photoluminescent imaging system for viewing one or more patterns of fluorescence emitted by fluorophors capable of being excited by light of an excitation type and of producing light of an emitted type, wherein at least a portion of said emitted type is of a wavelength and polarization different from said excitation type, said system comprising:

a) a non-laser light producing element that produces light, at least a portion of which is light of said excitation type;

b) a first optical polarization filter positioned between said light producing element and said fluorophors, wherein said first filter is capable of transmitting polarized light of said excitation type having a first polarization orientation and capable of preventing transmission of light from the light-producing element having a polarization orientation different than said first polarization orientation;

c) a second optical polarization filter positioned in optical communication with said fluorophors, wherein said second filter is capable of transmitting polarized light of said emitted type having a second polarization orientation and preventing transmission of light of said excitation type and wherein said second polarization orientation is different than that of said first orientation; and d) a third optical filter positioned in optical communication with said fluorophors, wherein the third optical filter is capable of transmitting light of wavelength of said emitted type from said fluorophors and of preventing transmission of light of wavelength of said excitation type.

said system being constructed and arranged such that patterns of fluorescence, emitted by said fluorophors, of wavelengths different than that of light of said excitation type, are viewable.

66. A visible light photoluminescent imaging system for viewing one or more patterns of fluorescence emitted by fluorophors capable of being excited by light of an excitation type and of producing light of an emitted type, wherein at least a portion of said emitted type is of a wavelength and polarization different from said excitation type, said system comprising: a) a non-laser light producing element that produces light, at least a portion of which is light of said excitation type;

b) a first optical polarization filter positioned between said light producing element and said fluorophors, wherein said first filter is capable of transmitting polarized light of said excitation type having a first polarization orientation and capable of preventing transmission of light from the light-producing element having a polarization orientation different than said first polarization orientation;

c) a second optical polarization filter positioned in optical communication with said fluorophors, wherein said second filter is capable of transmitting polarized light of said emitted type having a second polarization orientation and preventing transmission of light of said excitation type and wherein said second polarization orientation is different than that of said first orientation; and d) a third optical filter positioned between said light producing element and said fluorophors, wherein the third optical filter is capable of transmitting light having a wavelength of said excitation type from said light producing element and of preventing transmission of light having a wavelength of said emitted type;

said system being constructed and arranged such that patterns of fluorescence, emitted by said fluorophors, of wavelengths different than that of light of said excitation type, are viewable.

67. A visible light fluorescence imaging system for viewing one or more patterns of fluorescence emitted by fluorophors or a material containing fluorophors, capable of being excited by light of an excitation type and capable of emitting light of an emitted type, wherein at least a portion of said emitted type is of a wavelength different from said excitation type, said system comprising:

a) at least one blue, fluorescent lamp that produces light, at least a portion of which is capable of exciting said fluorophors, wherein said fluorescent lamp has a maximal output at about 450 nm;

b) a blue optical filter positioned between said fluorescent lamp and said fluorophors that is capable of transmitting light of said excitation type and of preventing transmission of light of said emitted type, wherein the blue optical filter has an absorbance greater than about 3 for light having a wavelength greater than about 550 nm; and c) an amber optical filter positioned in optical communication with said fluorophors, that is capable of transmitting light of said emitted type from said fluorophors and of preventing transmission of said excitation light, wherein said amber optical filter has an absorbance greater than about 3 for light having a wavelength less than about 540 nm;

said system being constructed and arranged such that patterns of fluorescence emitted by said fluorophors are viewable.

68. The visible light fluorescence imaging system of claim 67 wherein each fluorescent lamp has a nominal power consumption of about 9 W.

69. The visible light fluorescence imaging system of claim 67 wherein each fluorescent lamp has a nominal power consumption of about 28 W.

70. The visible light fluorescence imaging system of claim 67 wherein the optical filters have a transmission surface area ranging from about 19 cm to about 14,800 cm$^2$.

71. A visible light fluorescence imaging system for viewing one or more patterns of fluorescence emitted by fluorophors or a material containing fluorophors, capable of being excited by light of an excitation type and capable of emitting light of an emitted type, wherein at least a portion of said emitted type is of a wavelength different from said excitation type, said system comprising:

a) at least one blue light emitting diode that produces light, at least a portion of which is capable of exciting said fluorophors, wherein said light emitting has a maximal output at about 470 nm, b) a blue optical filter positioned between said light emitting diode and said fluorophors that is capable of transmitting light of said excitation type and of preventing transmission of light of said emitted type, wherein the blue optical filter has an absorbance greater than about 3 for light having a wavelength greater than about 550 nm; and c) an amber optical filter positioned in optical communication with said fluorophors, that is capable of transmitting light of said emitted type from said fluorophors and of preventing transmission of said excitation light, wherein said amber optical filter has an absorbance greater than about 3 for light having a wavelength less than about 540 nm.

said system being constructed and arranged such that patterns of fluorescence emitted by said fluorophors are viewable.

72. A visible light photoluminescent imaging system for viewing one or more patterns of fluorescence emitted by fluorophors, capable of being excited by light of an excitation type and capable of emitting light of an emitted type, wherein at least a portion of said emitted type is of a wavelength different from said excitation type, said system comprising:

a) a non-laser light source comprising a light producing element that produces light, at least a portion of which is capable of exciting said fluorophors, and a first optical filter positioned between said light producing element and said fluorophors that is capable of transmitting light of said excitation type and of preventing transmission of light of said emitted type;

b) a second optical filter positioned in optical communication with said fluorophors, wherein said second optical filter is capable of transmitting light of said emitted type from said fluorophors and of preventing transmission of said excitation light; and c) at least one additional optical filter positioned in optical communication with said second optical filter, wherein said additional optical filter is capable of transmitting light of said emitted type from said fluorophors and of preventing transmission of infrared light;

said system being constructed and arranged such that patterns of fluorescence emitted by said fluorophors are viewable.

73. A visible light photoluminescent imaging system for viewing one or more patterns of fluorescence emitted by fluorophors, capable of being excited by light of an excitation type and capable of emitting light of an emitted type, wherein at least a portion of said emitted type is of a wavelength different from said excitation type, said system comprising:

a) a non-laser light source comprising a light producing element that produces light, at least a portion of which is capable of exciting said fluorophors, and a first optical filter positioned between said light producing element and said fluorophors that is capable of transmitting light of said excitation type and of preventing transmission of light of said emitted type;

b) a second optical filter positioned in optical communication with said fluorophors, wherein said second optical filter is capable of transmitting light of said emitted type from said fluorophors and of preventing transmission of said excitation light; and c) at least one additional optical filter positioned in optical communication with said second optical filter, wherein said additional optical filter is capable of transmitting light of said emitted type from said fluorophors and of preventing transmission of light generated by fluorescence of said second optical filter;

said system being constructed and arranged such that patterns of fluorescence emitted by said fluorophors are viewable.

74. A visible light photoluminescent imaging system for viewing one or more patterns of fluorescence emitted by fluorophors, capable of being excited by light of an excitation type and capable of emitting light of an emitted type, wherein at least a portion of said emitted type is of a wavelength different from said excitation type, said system comprising:

a) a non-laser light source comprising a light producing element that produces light, at least a portion of which is capable of exciting said fluorophors, and a first optical filter positioned between said light producing element and said fluorophors that is capable of transmitting light of said excitation type and of preventing transmission of light of said emitted type, wherein said first filter serves as a direct support for said material containing said fluorophors; and b) a second optical filter positioned in optical communication with said fluorophors, wherein said second optical filter is capable of transmitting light of said emitted type from said fluorophors and of preventing transmission of said excitation light;

said system being constructed and arranged such that patterns of fluorescence emitted by said fluorophors are viewable.

* * * * *

UNITED STATES PATENT AND TRADEMARK OFFICE
CERTIFICATE OF CORRECTION

PATENT NO. : 6,512,236 B2
DATED : January 28, 2003
INVENTOR(S) : Seville

It is certified that error appears in the above-identified patent and that said Letters Patent is hereby corrected as shown below:

Column 2,
Line 28, please replace "Avisible" with -- A visible --.

Column 21,
Line 9, please replace "Oreg." with -- OR --.

Column 26,
Line 63, after "300 seconds" please insert -- after the device was turned on --.

Column 30,
Line 49, please replace "transilluminator" with -- photoluminescent imaging system --.

Column 34,
Line 37, please replace "cm" with -- cm2 --.

Signed and Sealed this

Twenty-ninth Day of July, 2003

JAMES E. ROGAN
*Director of the United States Patent and Trademark Office*